United States Patent [19]

Ebersole et al.

[11] Patent Number: 6,037,127
[45] Date of Patent: Mar. 14, 2000

[54] METHOD FOR DETECTION OF NON-DENATURED NUCLEIC ACID FRAGMENTS

[75] Inventors: Richard C. Ebersole, Wilmington; Edwin R. Hendrickson, Hockessin; Mark S. Payne, Wilmington, all of Del.; Sandra Fitzpatrick-McElligott, Rose Valley, Pa.; William R. Majarian, Mt. Royal, N.J.; Jan A. Rafalski, Wilmington, Del.

[73] Assignee: E. I. du Pont de Nemours and Company, Wimington, Del.

[21] Appl. No.: 08/979,269

[22] Filed: Nov. 26, 1997

Related U.S. Application Data

[63] Continuation-in-part of application No. 08/863,265, May 27, 1997, abandoned, which is a continuation of application No. 08/530,795, Sep. 20, 1995, abandoned, which is a continuation of application No. 08/221,769, Mar. 31, 1994, abandoned.

[51] Int. Cl.[7] .............................. C12Q 1/68; C12P 19/34
[52] U.S. Cl. ................................ 435/6; 435/91.2; 436/94
[58] Field of Search .............................. 435/6, 91.1, 91.2, 435/183; 436/94; 536/23.1, 24.3, 24.33, 25.1; 935/8, 76, 77

[56] References Cited

U.S. PATENT DOCUMENTS

| | | | |
|---|---|---|---|
| 4,189,304 | 2/1980 | Adams, Jr. et al. | 23/230 B |
| 4,740,468 | 4/1988 | Weng et al. | 435/7 |
| 5,075,078 | 12/1991 | Osikowicz et al. | 422/56 |
| 5,126,239 | 6/1992 | Livak et al. | 435/6 |
| 5,200,313 | 4/1993 | Carrico | 435/6 |
| 5,310,650 | 5/1994 | McMahon et al. | 435/6 |
| 5,369,007 | 11/1994 | Kidwell | 435/7.9 |

FOREIGN PATENT DOCUMENTS

| | | |
|---|---|---|
| 2034313 | 7/1991 | Canada . |
| 0 170 746 | 2/1986 | European Pat. Off. ..... G01N 33/543 |
| 0 237 833 | 9/1987 | European Pat. Off. ......... C12Q 1/68 |
| 0 306 772 | 3/1989 | European Pat. Off. ..... G01N 33/558 |
| 0 387 696 | 9/1990 | European Pat. Off. ......... C12Q 1/68 |
| 0 420 260 | 4/1991 | European Pat. Off. ......... C12Q 1/68 |
| 0 582 231 | 2/1994 | European Pat. Off. ..... G01N 33/558 |
| WO 88/06189 | 8/1988 | WIPO ............................. C12Q 1/68 |
| WO 88/08534 | 11/1988 | WIPO ........................ G01N 33/543 |
| WO 90/06374 | 6/1990 | WIPO ............................. C12Q 1/68 |
| WO 91/15769 | 10/1991 | WIPO ........................ G01N 33/543 |
| WO 92/12428 | 7/1992 | WIPO ............................ G01N 33/53 |
| WO 92/17609 | 10/1992 | WIPO ............................. C12Q 1/68 |
| WO 93/07292 | 4/1993 | WIPO . |

OTHER PUBLICATIONS

Sommer and Tautz, "Minimal homology requirements for PCR primers," Nucleic Acids Research, vol. 17, No. 16, p. 6749, 1989.
Corti, A. et al., "Rapid and Simple DNA Detection by Hybridization on Absorbent Filters", Nucleic Acids Research, 19(6), 1351, Jan. 2, 1991.
Corti, A. et al., "A Rapid Method for Monitoring DNA Labelling Reactions with Haptens", Journal of Immunological Methods, 134, 81–86, 1990.
Williams et al., Nucleic Acids Research, 18(22), 6531–6535, 1990.
Lion et al., Analytical Biochemistry, 188, 335–337, 1990.
Sommer and Tautz, Nucleic Acids Research, 17(16), 6749, 1989.
Calvin P.H. Vary, "Triple–Helical Capture Assay for Quantitation of Polymerase Chain Reaction Products," Clin. Chem., 38(5), 687–694, 1992.
Sigma Molecular Biology Catalog, p. 54, 1989.
Lion et al., "Nonradioactive Labeling of Probe with Diogoxigenin by Polymerase Chain Reaction,", Analytical Biochemistry, 188, 335–337, 1990.

Primary Examiner—Kenneth R. Horlick

[57] ABSTRACT

A method for detecting the presence of a nucleic acid analyte in a test sample is provided in which a test sample is contacted with a test strip of a chromatographic bibulous porous material which is capable of moving the test sample laterally along the test strip by capillary migration to ultimate capture by a moiety in a specific capture zone.

11 Claims, 13 Drawing Sheets

Lateral Flow Detection
(Denatured vs Nondenatured)

AV = Avidin
SA = Streptavidin
XA = Extra Avidin

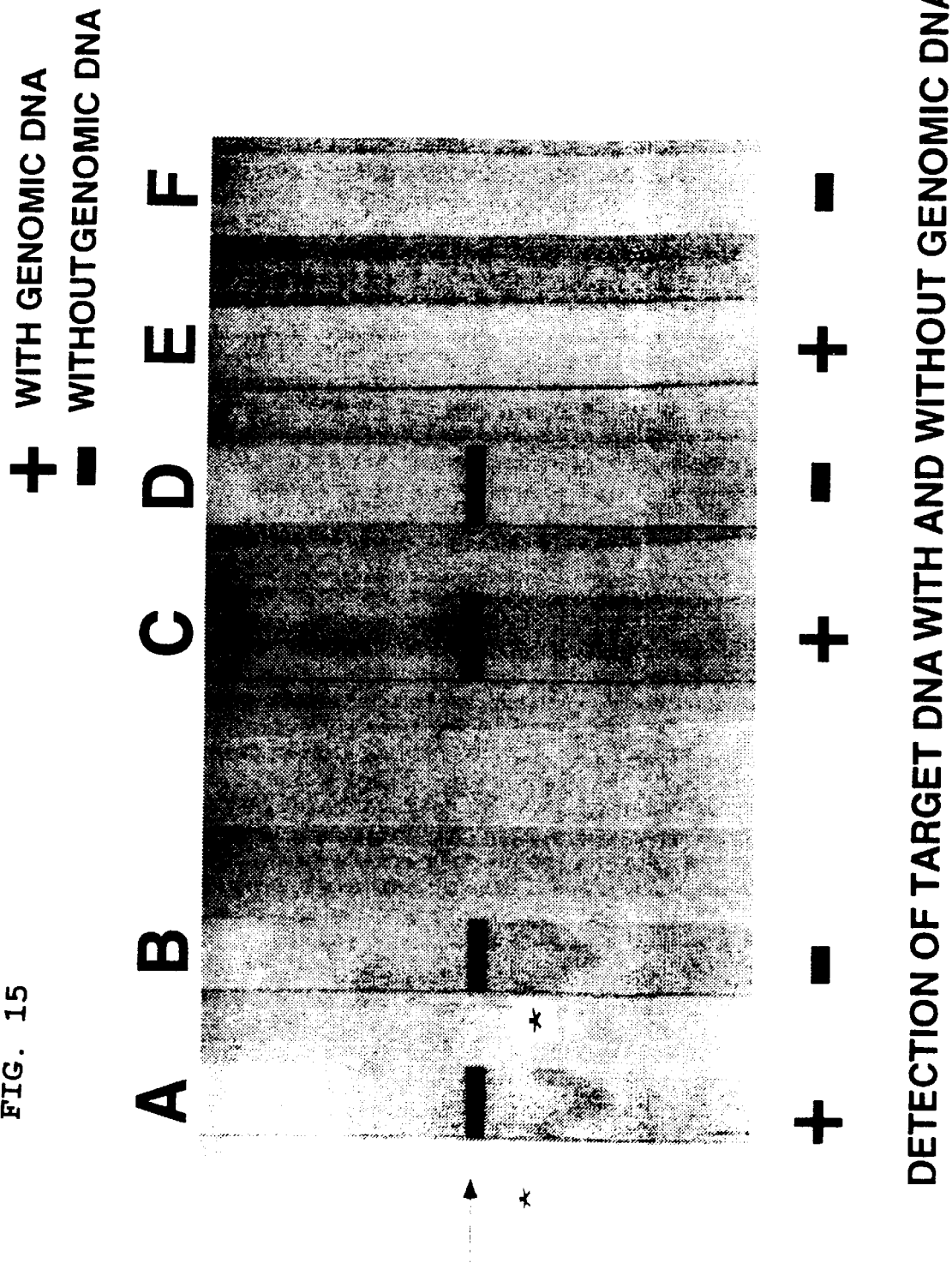

METHOD FOR DETECTION OF NON-DENATURED NUCLEIC ACID FRAGMENTS

This application is a continuation-in-part of application Ser. No. 08/863,265, filed on May 27, 1997, abandoned, which is a file wrapper continuation of 08/530,795, filed on Sep. 20, 1995, abandoned, which is a file wrapper continuation of Serial No. 08/221,769, filed on Mar. 31, 1994, abandoned.

FIELD OF INVENTION

The present invention relates to the identification of nucleic acid fragments within a continuous lateral flow assay system.

BACKGROUND OF THE INVENTION

Methods for the rapid and sensitive detection of nucleic acid fragments are gaining importance in the medical, environmental and food diagnostic industries as well as areas relying on genetic analysis such as forensics. Because of their specificity, nucleic acid sequences are being relied upon for the positive identification of disease as well as for indicating the presence of contaminating bacteria and other microorganisms.

Typically the identification of nucleic acid fragments has involved time consuming methods such as restriction enzyme analysis followed by gel electro-phoresis and staining. Such methods lack sensitivity and are not easily adaptable for rapid detection and field use.

With the development of techniques for rapid nucleic acid amplification involving thermostable nucleic acid amplifying enzymes (ligases, polymerases, transferases, etc.) such as the polymerase chain reaction (PCR), ligase chain reaction (LCR) and the relatively new strand displacement amplification (SDA), it is now possible to generate multiple copies of nucleic acid analytes that have been heretofore undetectable. Modifications of these techniques have allowed for the generation of ligand-labeled nucleic acid fragments which has in turn permitted the development of new, highly sensitive nucleic acid detection assays.

Recently developed assays use labeled nucleic acid fragments immobilized on various supports for detection of the desired fragment by an enzyme or fluorescent reporter. EP 437774 discloses single or double-stranded nucleic acids containing one or more detectable groups and two or more immobilization-facilitating groups in one strand. A target nucleic acid is amplified by a polymerase chain reaction forming multiple copies of a complementary nucleic acid containing detection or immobilizing groups. The resulting nucleic acid is immobilized on a solid phase and the detectable groups are detected. The immobilization-facilitating groups are derived from haptens such as digoxigenin and vitamins such as biotin, as well as antigens, antibodies, and lectins. The detectable groups are selected from radio-isotopes, fluorescent dyes, chromophores or indirectly-detectable groups such as digoxigenin and enzyme reporters.

EP 420260 teaches a hybridization method for the assay of nucleic acids involving a capture probe immobilized on a solid support to bind a labelled target nucleic acid sequence. A labelled target nucleic acid is amplified from a biological sample where the target is hybridized with at least one oligonucleotide capture probe having a nucleic acid sequence complementary to the target sequence, and where the capture probe is bound to a polystyrene solid support. Hybridization takes place in the presence of guanidine thiocyanate and the label may be biotin in the form of biotin-11-dUTP incorporated by Taq polymerase during polymerase chain reaction (PCR) amplification. The biotin label is detected by the addition of avidin or streptavidin complexed with horseradish peroxidase (HRP), alkaline phosphatase, beta-galactosidase, luciferase, fluorescein or Texas red. The HRP is detected with a chromogenic agent and $H_2O_2$.

In a similar method, EP 447464 discloses a method for the capture and detection of ligand labeled DNA. The method involves capturing ligand containing amplified target DNA on a solid substrate having an immobilized binding reagent for the ligand. The binding reagent is a DNA binding protein, such as glutathione-5-transterase (GST)-GCN4 or Tyr R and detection of the captured DNA is accomplished with a second ligand such as biotin where detection is accomplished via an avidin/peroxidase system.

Hornes et al., in WO 9217609 teach a method of detecting bacterial cells using PCR of bacterial nucleic acids using ligand labeled nested primers. The method comprises lysing a mixture of bacterial cells and liberating DNA and/or RNA followed by amplifying DNA characteristic of the cells by PCR and detecting the amplified DNA. The PCR is carried out using nested primers, where one of the inner nested primers carries a biotin molecule and the other inner primer carries digoxigen.

The above cited methods are useful for detection of amplified nucleic acid analytes. However, they have several limitations including the need to perform the reactions by the sequential addition of reagents followed by multiple washings and the inability to assay for multiple analytes.

Methods of nucleic acid detection involving fewer washing steps and immobilization on a porous membrane have also been disclosed. Corti et al. (Nuc. Acids Res., 19, 1351 (1991) teach a method for the detection of DNA that is based on hybridization of target DNA with digoxigenin-lableled probes on disposable filters. The method involves prewetting the filter with buffer followed by addition of target DNA, addition of blocking reagent and hybridizing solution and finally the subsequent addition of digoxigenin-labelled DNA probe under hybridizing conditions. Detection of bound digoxigenin-DNA is carried out with alkaline phosphatase/anti-digoxigenin antibody conjugate and chomogenic substrates.

The method of Corti et al. is useful for detection of labeled DNA fragments, but is still hampered by the time consuming, sequential addition of reagents. A preferred method would derive benefit from a single addition of reagents and the elimination of washing steps.

The relative speed and specificity of immunoassays have lead to the development of test kits capable of rapid immunological diagnostic tests. Several of these immunoassays employ a lateral fluid flow system comprising a porous membrane material within which test reagents are located that are capable of reacting with analytes in a test solution as they are drawn down the membrane by capillary action.

Weng et al. (U.S. Pat. No. 4,740,468) disclose a method for determining the presence of an analyte in a sample involving contacting one end of a bibulous test strip with a test solution which contains the sample and a first member of a specific binding pair. The bibulous test strip is capable of being traversed by the test solution through capillary action. The first member of a specific binding pair is designed to specifically bind the analyte. The strip further contains a second member of a specific binding pair useful for concentrating and binding the first specific binding pair member at a small site on the strip. The detectable signal is produced in relation to the presence of the analyte in the test solution. The method of Weng et al. does not disclose or teach the detection of nucleic acids.

Similarly, May et al. (WO 8808534) disclose an analytical test device comprising a porous carrier material which contains a labelled binding reagent, specific for an analyte. This reagent is able to move freely within the carrier material. The strip also contains an unlabeled specific binding reagent for the same reagent which is immobilized in a detection zone on the carrier material. Liquid sample applied to the device is able to pick up labelled reagent and permeate the detection zone where it reacts with the unlabeled reagent and is immobilized for detection. A similar method is disclosed by Wood et al. (EP 170746) where an analyte is bound to a multiplicity of particles which are in turn adhered to a solid plastic support for detection and by Adams et al. (U.S. Pat. No. 4,189,304) who teach a method of detecting myoglobin in the presence of hemoglobin comprising a chromatographic medium and device.

The above cited immunological methods are useful for the detection and quantitation of immuno-reactive analytes. However, they do not teach the detection and identification of nucleic acid fragments.

In developing assays involving immunological reactions many factors must be considered. One consideration is to provide substantial differentiation between the observed signal resulting from signal label when bound as compared to unbound. Another consideration is to minimize interference from endogenous materials in the sample suspected of containing the compound of interest. Further considerations are the ease with which the observed signal can be detected and its ability to differentiate between concentrations in the concentration range of interest. Other factors include the ease of preparation of the reagents, the accuracy with which samples and reagent solutions must be prepared and measured, the storage stability of the reagents, the number of steps required in the protocol, and the proficiency and accuracy with which each of the steps must be performed. Therefore, in developing an assay for use by untrained personnel (such as assays to be performed in the home, in forensic medicine, by medical practitioners, or the like), the observed result should be minimally affected by variations in the manner in which the protocol is carried out or provide for simple techniques for performing the various steps.

There exists a need, therefore, for a method for the rapid, sensitive and facile identification of nucleic acid fragments that is readily adaptable for use in the field.

SUMMARY OF THE INVENTION

The present invention provides a method for detecting the presence of an nucleic acid analyte in a test sample comprising the steps of: (i) contacting the test sample with a first end of a test strip comprising a chromatographic material capable of moving the test sample laterally from the first end to the second end of the test strip by capillary migration and at least one capture moiety irreversibly affixed to the test strip at a specific capture zone; (ii) allowing the test sample time to traverse at least a portion of the test strip whereby the nucleic acid analyte is captured and immobilized in the capture zone; (iii) contacting the test strip with a signal-generating substance such that the signal-generating substance reacts with a reporter conjugate that is located either within the nucleic acid analyte or bound to the nucleic acid analyte to produce a detectable signal at the capture zone; and (iv) comparing the detectable signal at the capture zone with a signal detectable at a portion of the test strip other than at the capture zone.

The invention further provides a method whereby the reporter conjugate comprises a reporter moiety linked to a member of a binding pair, an antibody or a nucleic acid, the reporter moiety being a fluorescent molecule, an enzyme or a radioactive molecule capable of producing a detectable signal.

Optionally, the invention provides a method whereby the nucleic acid analyte is immobilized at the capture zone of the test strip by hybridization to a nucleic acid capture reagent having a sequence complementary with a portion of the nucleic acid analyte.

Alternatively, the invention is a method for detecting the presence of a RAPD amplified nucleic acid analyte in a test sample comprising the steps of: (i) contacting the test sample with a first end of a test strip comprising a chromatographic material, the test strip having a specific capture zone in which the RAPD amplified nucleic acid analyte is immobilized; (ii) contacting the test strip with a solution containing a detection probe, the detection probe comprising a base sequence complementary with the RAPD amplified analyte; (iii) allowing said solution time to traverse at least a portion of the test strip whereby the detection probe and the RAPD amplified nucleic acid analyte hybridize; and (iv) contacting the test strip with a signal generating substance such that the signal generating substance reacts with a reporter conjugate located either within the detection probe or bound to the detection probe to produce a detectable signal at the capture zone.

The present invention is widely useful for rapid identification of nucleic acid fragments. Applications include human and veterinary medicine, agriculture, and food science, among others. In particular, the method can be used to detect and identify etiological agents such as bacteria and viruses, to screen microbes for antibiotic resistance, and to detect malignant cells.

BRIEF DESCRIPTION OF THE DRAWINGS & SEQUENCE LISTING

FIGS. 1A and B, illustrate the lateral flow detection of a bifunctional nucleic acid analyte with two reactive ligands, one of which is capable of reacting with the capture reagent where the other is capable of reacting with the conjugate reporter.

FIGS. 2A and B, illustrate a typical lateral flow system for the detection of a nucleic acid analyte where the analyte is captured in the capture zone by hybridizing to a capture nucleic acid of complementary sequence.

FIGS. 3A and B, illustrate the lateral flow detection of a nucleic acid analyte where the reporter molecule is incorporated into the analyte and capture is effected by hybridization with a capture nucleic acid.

Figure 6:
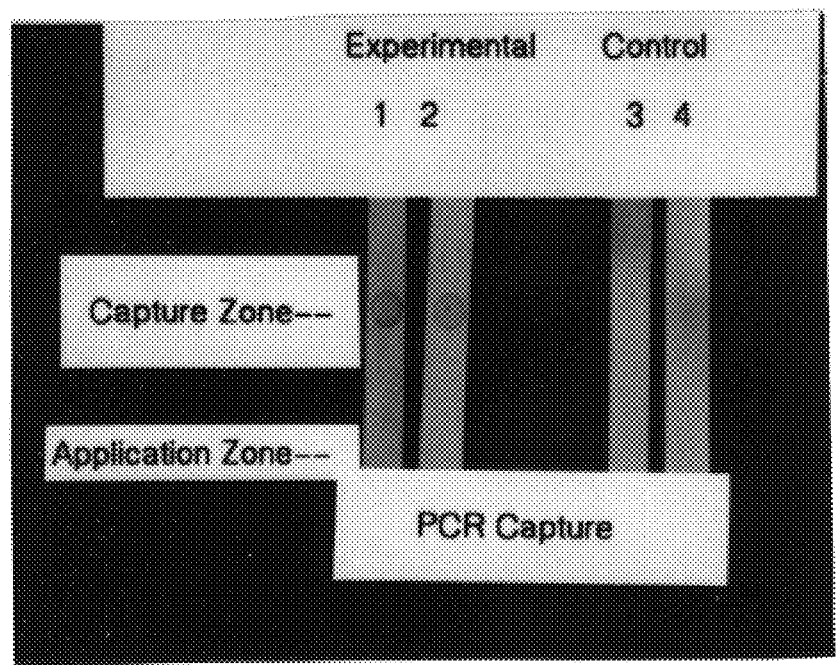

FIG. 6 is a photographic representation of the positive detection of dnak promoter by hybridization to a PCR generated biotin (lane 1) and digoxigenin (lane 2) labeled complementary sequence. Negative controls (lanes 3 and 4) show the lack of a colorimetric reaction to non-complementary PCR DNA targets.

Figure 7:
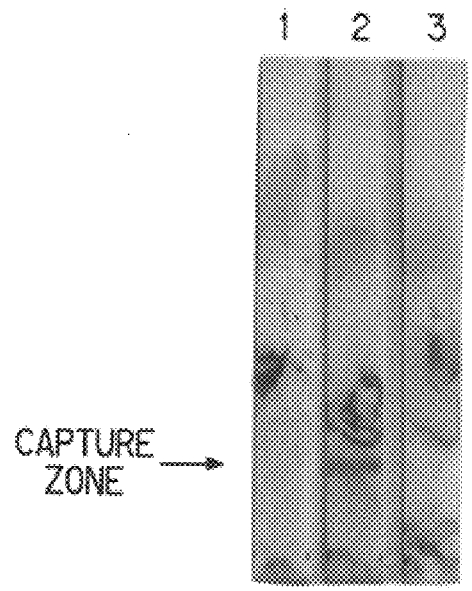

FIG. 7 is a photographic representation of the positive detection of aprE bacterial DNA by a lateral flow nucleic acid analyte detection system, employing solution phase nucleic acid hybridization.

Figure 8:
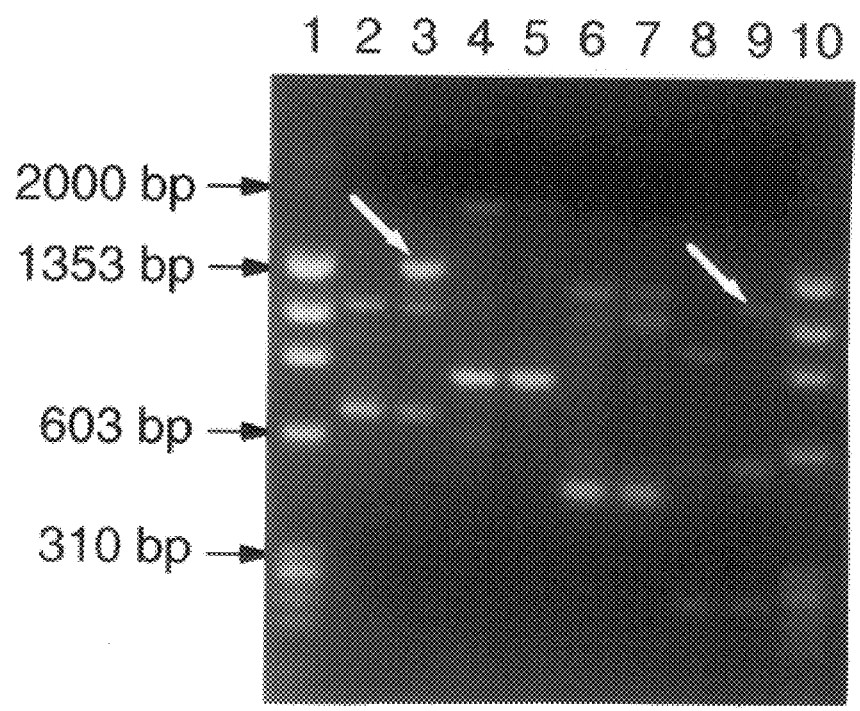

FIG. 8 is an electrophoretic separation of RAPD amplified DNA from *B. napus* showing two polymorphic bands in lanes 3 and 9.

Figure 9A:
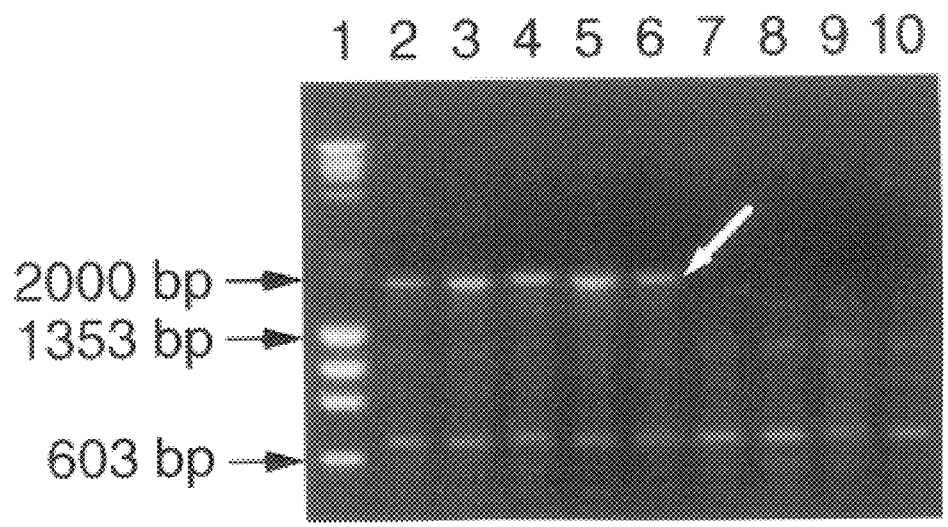

FIG. 9A shows an electrophoretic separation of RAPD amplified DNA from soybean showing a polymorphic band in lane 6.

Figure 9B:
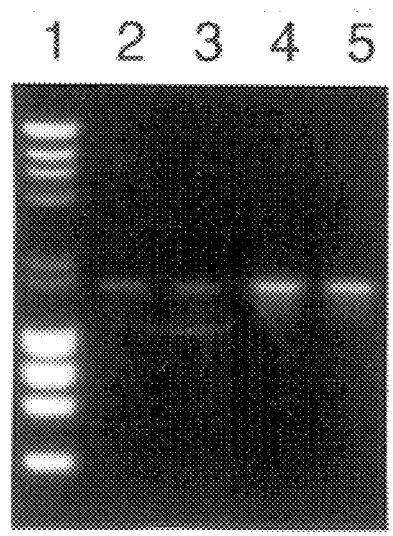

FIG. 9B shows an electrophoretic separation of RAPD amplified DNA from soybean where lanes 2 and 3 show the DNA excised from Panel A, lane 6, biotinylated and re-amplified. Panel B, lanes 4 and 5, show the DNA from lane 6, Panel A, fluoresceinated and re-amplified.

Figure 10A:
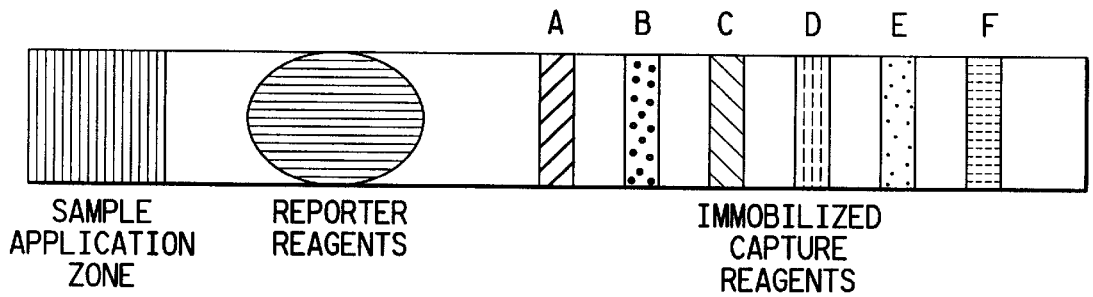

FIGS. 10A and B, illustrate test strips capable of capturing multiple analytes by specific nucleic acid or antibody affinity capture reagents.

Figure 11:
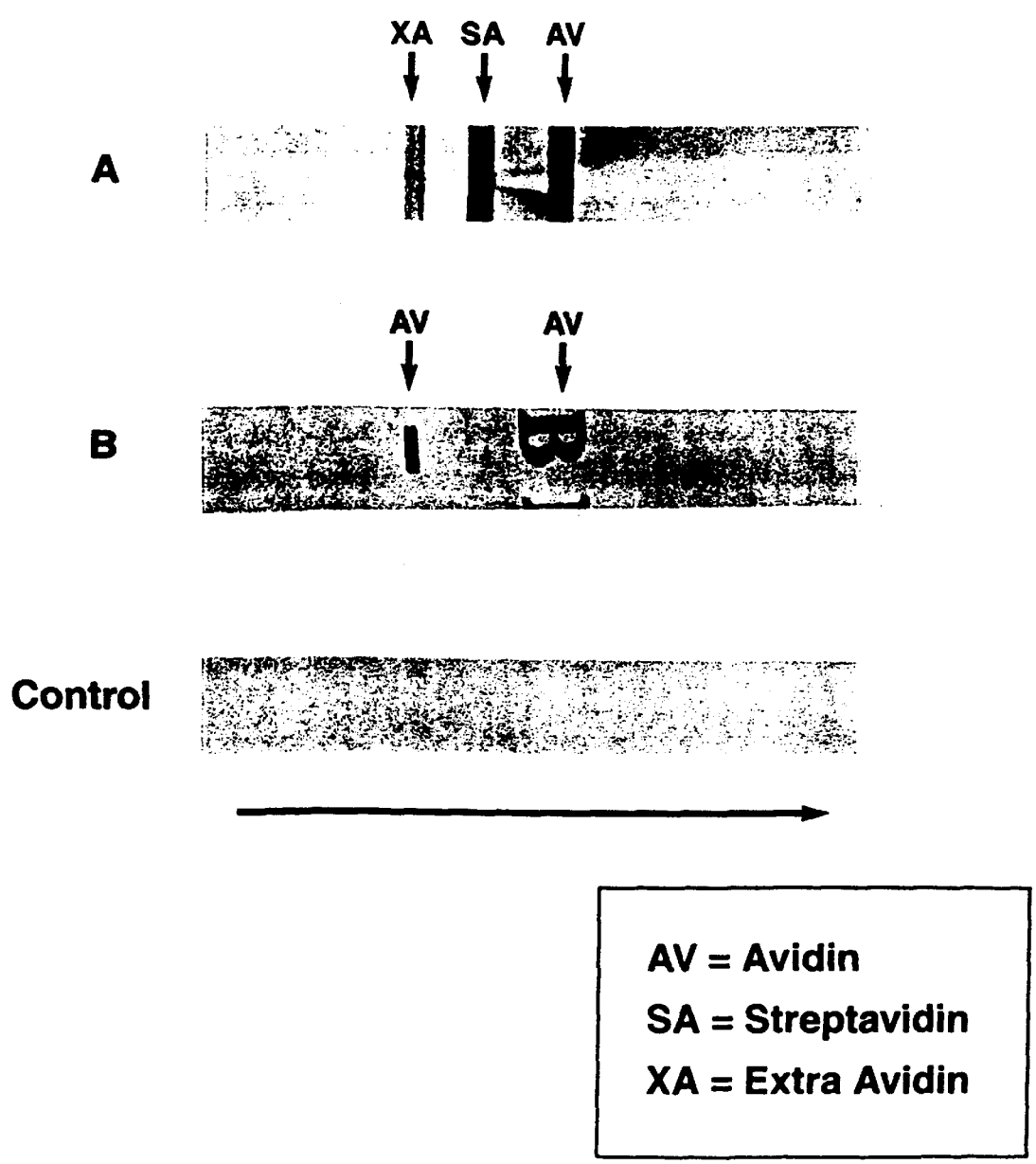

FIG. 11 is a test strip showing the capture of undenatured, ligand labeled double-stranded PCR product in three different capture zones.

Figure 12:
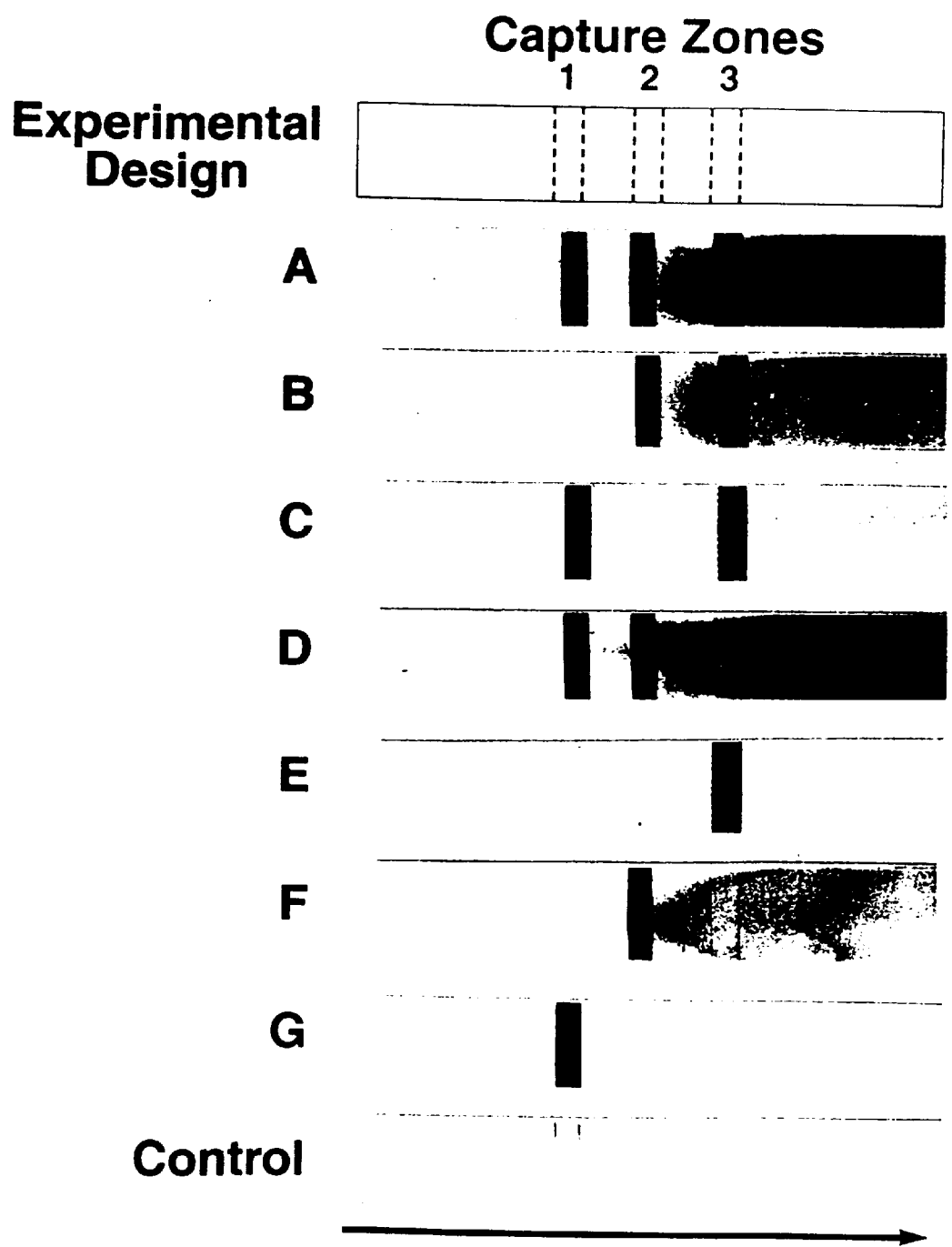

FIG. 12 show test strips containing PCR amplification products captured by hybridization in a multianalyte format.

Figure 13:
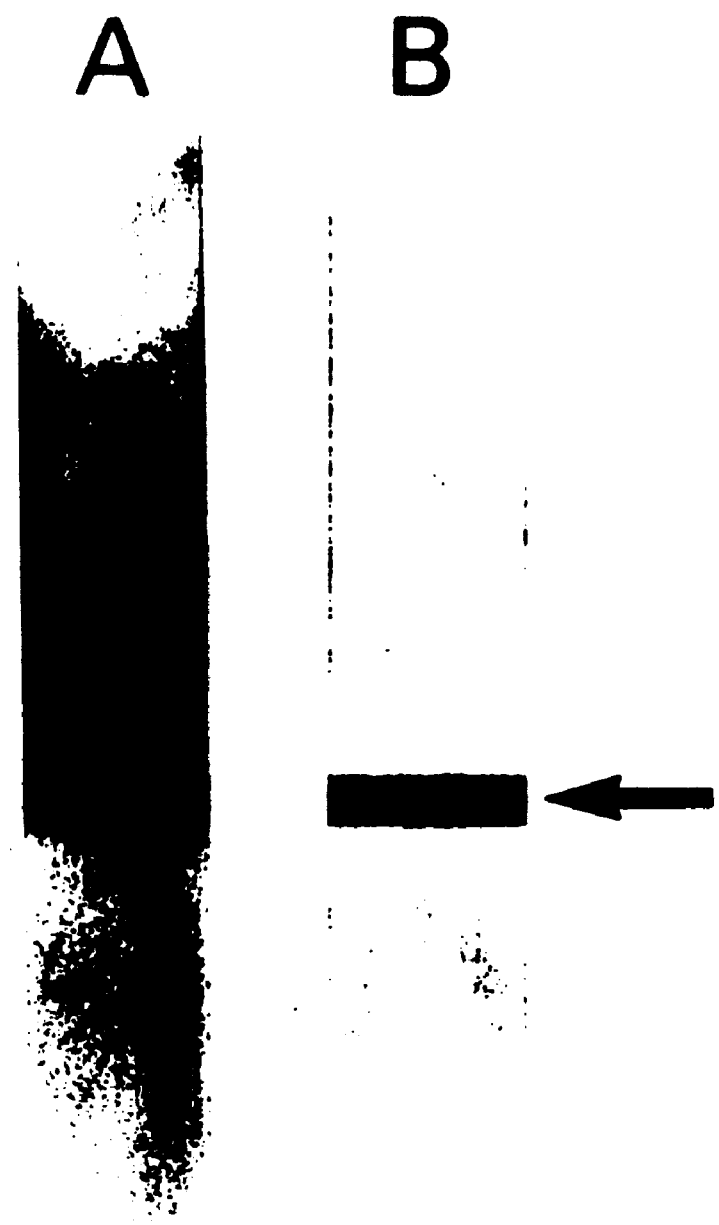

FIG. 13 is a test strip showing the Detection of the Venezuelan Equine Encephalitis 289 bp PCR products.

Figure 14:
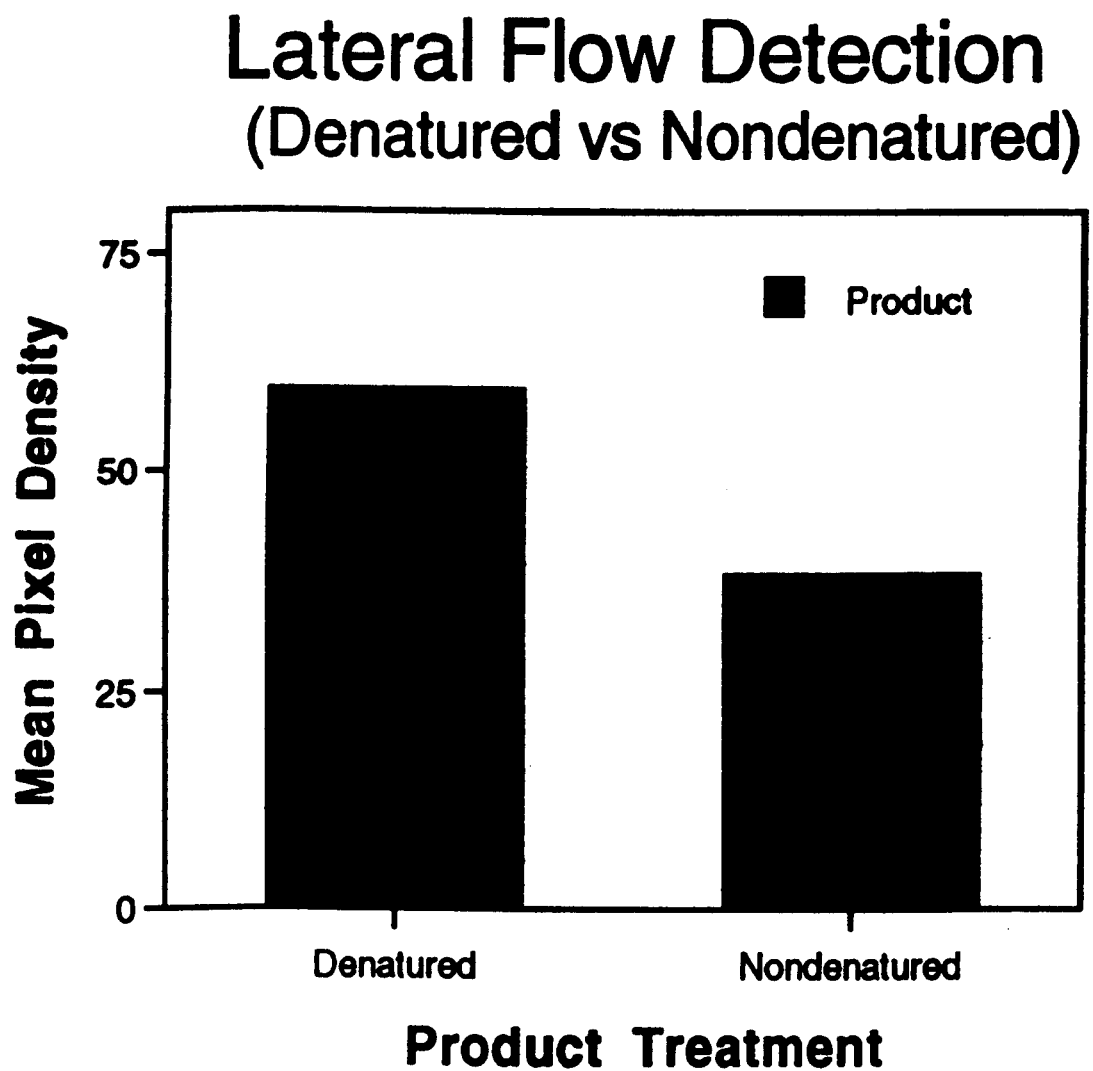

FIG. 14 is a plot showing the mean pixel density of the capture zones shown in FIG. 13 minus strip background.

FIG. 15 are test strips showing the Detection of the 99 base fragment target DNA with and without genomic DNA at the reaction zone containing specific immobilized probes.

The following sequence descriptions and sequences listings attached hereto comply with the rules governing nucleotide and/or amino acid sequence disclosures in patent applications as set forth in 37 C.F.R § 1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence for the *B. subtilis* aprE target DNA.

SEQ ID NO:2 is the 5' primer for the amplification of the *B. subtilis* aprE target DNA.

SEQ ID NO:3 is the 3' primer for the amplification of the *B. subtilis* aprE target DNA.

SEQ ID NO:4 is the sequence of the *E. coli* dnak gene.

SEQ ID NO:5 is the 5' primer for the amplification of the *E. coli* dnak gene.

SEQ ID NO:6 is the 3' primer for the amplification of the *E. coli* dnak gene.

SEQ ID NO:7 is a synthetic oligonucleotides having homology to the 5' end of the *E. coli* dnak promoter.

SEQ ID NO:8 is a synthetic oligonucleotides having homology to the 3' end of the *E. coli* dnak promoter.

SEQ ID NO:9 is a RAPD primer used for the amplification of *B. napus* DNA.

SEQ ID NO:10 is a RAPD primer used for the amplification of soybean DNA.

SEQ ID NO:11 is a biotinylated primer for the amplification and labeling of *B. napus* DNA.

SEQ ID NO:12 is a fluorescent primer for the amplification and labeling of soybean DNA.

SEQ ID NO:13 is a biotinylated primer for the amplification and labeling of soybean DNA.

SEQ ID NO:14 is a 99 mer base Target DNA used for the detection of double-stranded DNA without hybridization.

SEQ ID NO:15 is the 5' primer used for the amplification of the 99 mer base Target DNA used for the detection of double-stranded DNA without hybridization.

SEQ ID NO:16 is the 3' primer used for the amplification of the 99 mer base Target DNA used for the detection of double-stranded DNA without hybridization.

SEQ ID NO:17 is a single stranded capture probe complementary to the *B. subtilis* apr target DNA (SEQ ID NO:18).

SEQ ID NO:18 is the *B. subtilis* apr target DNA.

SEQ ID NO:19 is a single stranded capture probe complementary to the *E. coli* dnaK target DNA (SEQ ID NO:20).

SEQ ID NO:20 is the *E. coli* dnak target DNA.

SEQ ID NO:21 is a single stranded capture probe complementary to the the 99 base target DNA (SEQ ID NO:14).

SEQ ID NO:22 is a 5' primer used for the amplification of the Venezuelan Equine Encephalitis gene to yield a 707 base product.

SEQ ID NO:23 is a 3' primer used for the amplification of the Venezuelan Equine Encephalitis gene to yield a 707 base product.

SEQ ID NO:24 is a 5' primer used for the amplification of the Venezuelan Equine Encephalitis gene to yield a 289 base product.

SEQ ID NO:25 is a 3' primer used for the amplification of the Venezuelan Equine Encephalitis gene to yield a 289 base product.

SEQ ID NO:26 is a capture probe for hybridization to Venezuelan Equine Encephalitis target DNA.

SEQ ID NO:27 is a capture probe for hybridization to 99 base target DNA.

DETAILED DESCRIPTION OF THE INVENTION

The present invention provides a method for the detection of nucleic acids which relies on the incorporation of at least one reactive ligand into a nucleic acid analyte by standard amplification means and the concentration and detection of that analyte utilizing a lateral flow chromatographic system.

As used herein the following terms may be used for interpretation of the claims and specification.

A "fragment" constitutes a fraction of the DNA sequence of the particular region.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The term "target nucleic acid" will refer the nucleic acid fragment targeted for amplification or replication and subsequent detection. Sources of target nucleic acids will typically be isolated from organisms and pathogens to be identified by the instant method such as viruses and bacteria. Additionally it is contemplated that targets may also be from synthetic sources. Target nucleic acids are amplified via standard replication procedures to produce nucleic acid analytes.

The term "analyte" or "nucleic acid analyte" will refer to a substance to be detected or assayed by the method of the present invention. Typical analytes may include nucleic acid fragments including DNA, RNA or synthetic analogs thereof. A nucleic acid analyte may incorporate one or more reactive ligands which may serve as members of a binding pair. Such ligands are incorporated into the analyte in such a manner as to enable the ligand to react with a second member of a binding pair. Ligands may be coupled either at the 3' end, the 5' end or at any point between the 3' and 5' ends of the nucleic acid analyte. Additionally, reporter moieties may also be incorporated into the nucleic acid analyte in a manner similar to ligand incorporation. It is also contemplated that the nucleic acid analyte may be ligand-free but will incorporate sequence segments complementary to nucleic acid fragments comprising other reagents within the assay system.

The term "test sample" will refer to any fluid sample potentially containing an analyte.

The term "test strip" will refer to a chromatographic-like medium upon which an assay may be preformed. The test strip will contain an "application zone" for the application of the test sample and an "capture zone" which contains an immobilized capture reagent or capture nucleic acid capable of capturing and immobilizing the nucleic acid analyte. The capture zone will typically have a surface area substantially less than the surface area of the strip and contain immobilized capture reagents or capture nucleic acids. The zone may be a dot, line, curve, band, pattern formed from dots, lines, curves, bands, or combinations thereof. Generally, the direction of traversal of the strip by the test solution will be transverse to the zone. Preferably, the signal produced at the capture zone has a sharp-edged distinctive pattern that provides a sharp contrast to signal produced at portions of the strip other than the zone. For example, the zone can be a printed display of an abbreviated name or names of the analyte or analytes in the test solution.

The term "capture moiety" will refer to any reagent capable of reacting with a reactive ligand. Capture reagents are typically immobilized in the capture zone of the test strip. Typically capture reagents are members of binding pairs as discussed above.

The term "capture nucleic acid" will refer to a nucleic acid which has a sequence complementary to a portion of the nucleic acid analyte. The capture nucleic acid may either be immobilized on the test strip in the region of the capture zone or may be used to hybridize with the nucleic acid analyte prior to introduction to the lateral flow system. The capture nucleic acid may optionally comprise immuno or affinity reactive ligands. The capture nucleic acid may be immobilized on the test strip either directly by vacuum transfer or other well known methods, or indirectly by the interaction of an incorporated ligand with a previously immobilized capture reagent. The capture nucleic acid functions to immobilize the nucleic acid analyte by hybridizing with it either as it passes through the capture zone on the test strip or prior to application to the system.

The term "ligand" or "reactive ligand" will refer to one member of a binding pair which has been incorporated into the nucleic acid analyte and may include but is not limited to antibodies, lectins, receptors, binding proteins or chemical agents.

The term "binding pair" includes any of the class of immune-type binding pairs, such as antigen/antibody or hapten/anti-hapten systems; and also any of the class of nonimmune-type binding pairs, such as biotin/avidin; biotin/streptavidin; folic acid/folate binding protein; complementary nucleic acid segments; protein A or G/immunoglobulins; and binding pairs which form covalent bonds, such as sulfhydryl reactive groups including maleimides and haloacetyl derivatives, and amine reactive groups such as isotriocyanates, succinimidyl esters and sulfonyl halides.

The term "reporter conjugate" refers to a conjugate comprising an enzyme, fluorescent molecule or radioactive label coupled to one member of a binding pair. Typically the member of the binding pair is an antibody, nucleic acid sequence or some immuno-reactive or affinity-reactive substance.

The term "analyte reporter complex" will refer to a complex between the nucleic acid analyte and the reporter conjugate.

The term "immobilized analyte reporter complex" refers to a complex formed between a nucleic acid analyte, a reporter conjugate and an immobilized capture reagent.

The term "immobilized hybrid analyte reporter complex" refers to a complex formed between a nucleic acid analyte, a reporter conjugate and an immobilized capture nucleic acid.

The term "nucleic acid replication composition" refers to a composition comprising the ingredients necessary for performing nucleic acid replication. Applicants contemplate that replication may be accomplished by any of several schemes known in this art, including but not limited to the polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor et al., *Proc. Acad. Sci. U.S.A.*, 82, 1074–1078 (1985)).

If the SDA methodology is employed, amplification may be accomplished using either one or two short primers containing a site for HincII digestion, an exonuclease deficient DNA polymerase, HincII restriction enzyme and the bases dGTP, dCTP, dTTP and deoxyadenosine 5'[$\alpha$-thio] triphosphate [dATPS]. The SDA protocol including the necessary materials is outlined in Walker et al., *Proc. Natl. Acad. Sci. U.S.A.*, 89, 392, (1992)

The term "deposit" or "deposition" means directed binding to a immobilized receptor. Such deposition may result for example, from formation of a covalent bond, direct binding to a solid matrix, or from a specific binding pair interaction.

"Signal generating substance" refers to material or materials capable of interacting with a reporter moiety to produce a detectable signal. Examples are MBT/BCIP for alkaline phosphatase, TMB/ABTS for HRP, or light for fluorphase.

The term "reporter", "reporter moiety", or "signal-generating reporter" refers to any reporter capable of detection via enzymatic means or energy emission; including, but not limited to, fluorescent moieties, chemiluminescent moieties, particles, enzymes, radioactive tags, or light emitting moieties or molecules.

The term "particle" refers typically to latex particles that are dyed, submicron and uniform, but also includes other particles that otherwise are capable of detection.

The term "detection probe" refers to a nucleic acid fragment complementary to a nucleic acid analyte comprising ligands or reporters used to detect the presence of the analyte after analyte-probe hybridization.

The term "primer" refers to a nucleic acid that is complementary to at least one strand of the targeted nucleic acid and whose purpose is to sponsor and direct nucleic acid replication of the targeted sequence. Primers are designed to be complementary to specific segments of the target or reference sequences, and may be used in combination with another primer, thus forming a "primer set" or "primer pair". Requirements for primer size, base sequence, complementarity and target interaction are discussed in the primer section of the detailed description of the invention. The term "primer", as such, is used generally herein by Applicants to encompass any sequence-binding oligonucleotide which functions to initiate the nucleic acid replication process; such replication processes may include, for example, PCR, LCR or other enzymatic reactions which employ single rather than multiple oligonucleotide initiators.

The phrase "replicated nucleic acid sequences" or "replicated sequences" or "amplified sequences" refers to any nucleic acid replication products produced within the assay scheme of the present invention, and is used within this context to include replicated target sequences.

The terms "bibulous material" or "chromatographic material" will refer to a porous material having pores of at least 0.1 mu, preferably at least 10.0 mu, which is susceptible to traversal by an aqueous medium in response to capillary force.

The term "signal producing system" will refer to a system comprising all of the reagents required to produce a measurable signal. The signal producing system provides a signal detectable by external means, normally by measurement of electromagnetic radiation or by visual examination. For the most part the signal producing system includes a chromophoric substrate and enzyme, where chromophoric substrates are enzymatically converted to dyes which absorb light in the ultraviolet or visible region, phosphors or fluorescers.

The term "RAPD" will refer to random amplified polymorphic DNA and "RAPD method" will refer to a method for the detection of genetic polymorphisms involving the amplification of target nucleic acids using primers of arbitrary sequence.

The present invention provides a method for the detection of nucleic acid fragment analytes via a lateral flow assay system. By "lateral flow" it is meant that a sample suspected of containing an analyte is placed on a test strip consisting of a bibulous, chromatographic material and the sample is wicked laterally through of the test strip by capillary action, coincidentally reacting with various reagents in the strip. The scope of the invention is not limited with respect to the direction of the sample movement through the test strip. Analytes of the present invention may incorporate immunoreactive or affinity reactive ligands functioning as members of binding pairs or may be ligand-free but having regions complementary to other nucleic acid reagents in the assay system. Additionally the present assay may rely on the incorporation of reporter molecules directly into the analyte sequence for detection as opposed to the use of a reporter conjugate.

Figure 1A:
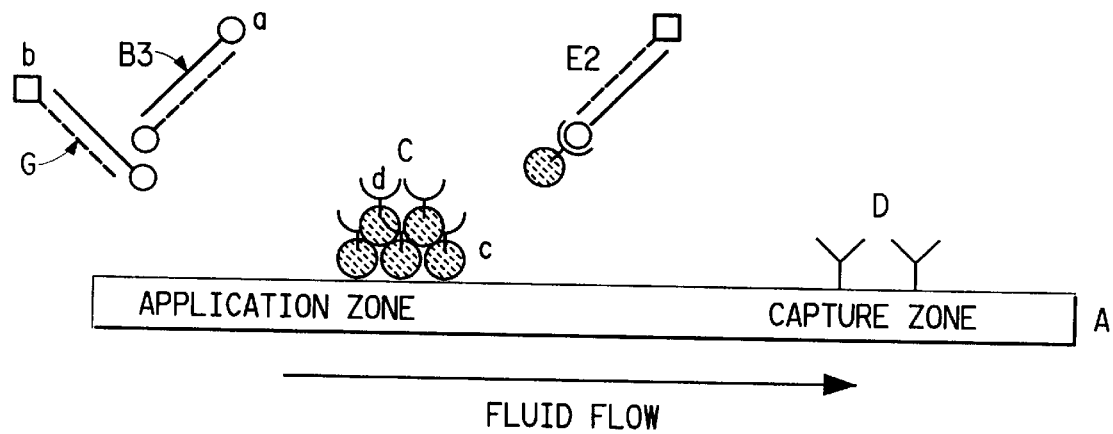
Figure 1B:
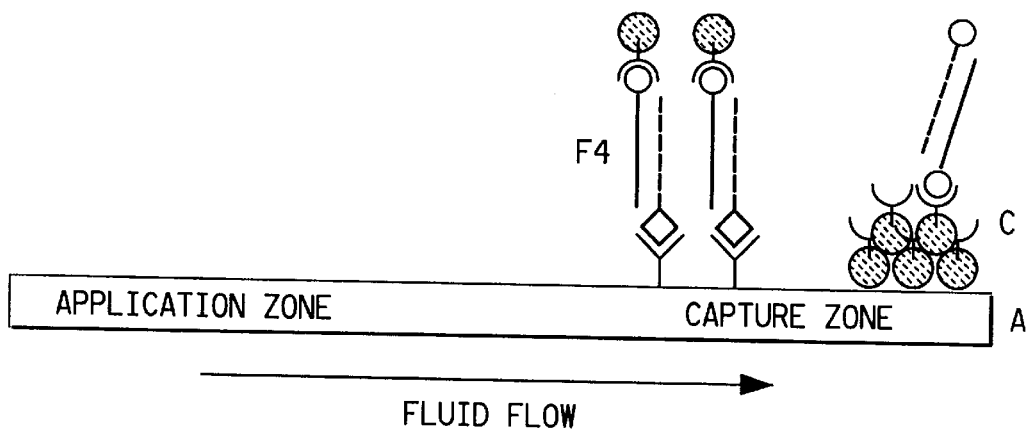

One preferred embodiment of the invention is illustrated in FIGS. 1A and 1B. The method illustrated in FIGS. 1A*a* and 1B demonstrates how nucleic acid analytes may be hybridized to the capture nucleic acid prior to immobilization and detection at the capture zone. Beginning with FIG. 1A and moving to FIG. 1B, the assay device comprises a test strip (A) made of a chromatographic, bibulous porous material which is capable of allowing fluid samples to traverse it in a lateral fashion by capillary action and containing an application zone which receives a liquid sample containing a nucleic acid analyte (B3) hybridized to a capture nucleic acid (G). In this embodiment the nucleic acid analyte (B3) and the capture nucleic acid (G) contain several immunoreactive or affinity-reactive ligands. Nucleic acids comprising ligands may be generated using ligand labeled dNTP's or ligand labeled primers and standard amplification procedures. Alternatively, it is contemplated that short primers of arbitrary sequence could also be used to generate the ligand labeled nucleic acid analytes or capture nucleic acids. Such primers would be particularly useful when the object is to detect polymorphisms in the target nucleic acid. In this embodiment the nucleic acid analyte (B3) is labelled with the reactive ligand (a), whereas the capture nucleic acid (G) is labelled with reactive-ligand (b). The test strip (A) contains a conjugate reporter (C) which comprises a reporter molecule (c) and a member of an immuno-reactive or affinity-reactive binding pair, (d). The binding pair member (d) is designed to react specifically with the reactive ligand (a) incorporated in the capture nucleic acid (G). The reporter molecule (c) is similar to that discussed above. The test strip (A) further contains an immobilized capture reagent (D), irreversibly affixed to the bibulous material and located in the capture zone. The capture reagent (D) is designed to bind to the reactive ligand (b), which is incorporated into the capture nucleic acid (G). When the test sample, containing the hybridized nucleic acid analyte (B3) and capture nucleic acid (G) has been applied to the application zone the sample is moved down the test strip (A) by capillary action over the conjugate reporter (C) in the direction of the capture zone. As the nucleic acid hybrid (B3, G) contacts the conjugate reporter (C) it is bound by the interaction of the reactive ligand (a) and the binding pair member (d) forming an analyte reporter complex (E2). Upon reaching the capture zone the analyte reporter complex (E2) is captured and immobilized by the interaction of the capture reagent (D) and the reactive ligand (b), forming an immobilized analyte reporter complex (F4). Continued movement of the sample fluid draws excess reagents and unbound analyte past the capture zone. In the case where the reporter molecule (c) is an enzyme, reaction buffer containing the enzyme substrate, cofactors and chromogens is added to the test strip (A) at the application zone after the excess reagents have moved past the capture zone. Interaction of the reporter enzyme with its substrate catalyses a reaction which results in a detectable signal.

The sequence of events outlined in FIGS. 1A and 1B may be altered without affecting the detection of the nucleic acid analyte. For example, it would be possible to adapt the current embodiment so that analytes containing reactive ligand (b) would be first allowed to be immobilized at the capture zone, followed by hybridization with a capture nucleic acid comprising reactive ligand (a), optionally, additionally comprising the reporter conjugate.

It will be appreciated that the embodiment illustrated in FIGS. 1A and B are not limited to the detection a single nucleic acid analyte. Rather, it is contemplated that a multiplicity of analytes could be detected in a single assay by allowing for a variety of reactive ligands, reporter conjugates and capture reagents all capable of specific and exclusive interaction.

Figure 2A:
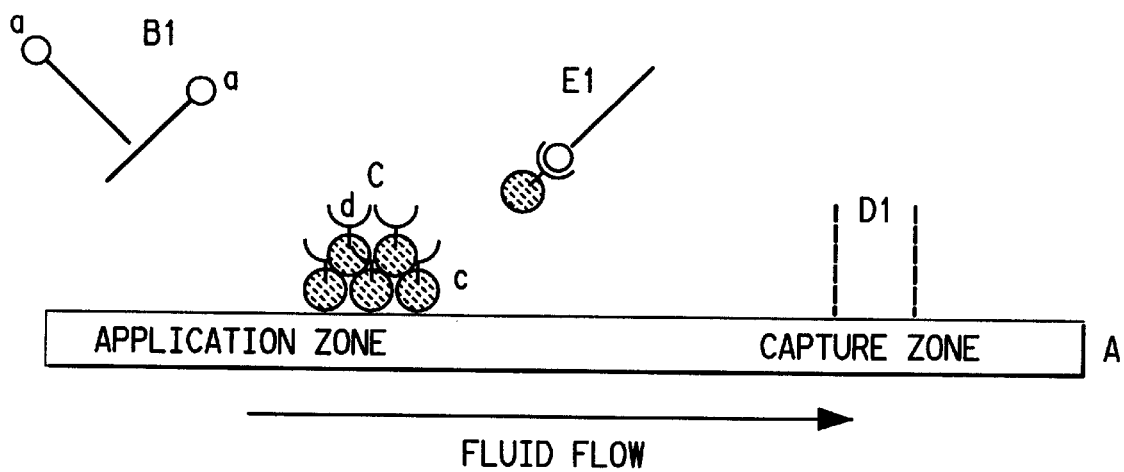
Figure 2B:
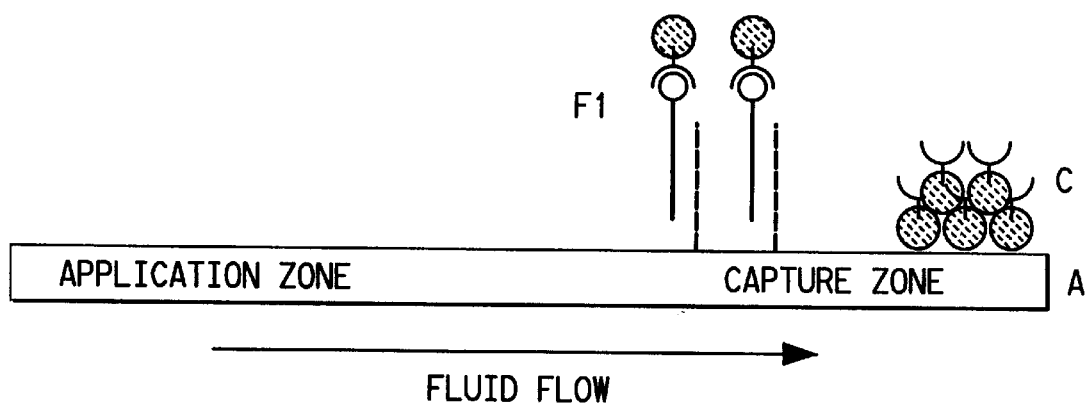

An alternate embodiment of the invention is illustrated in FIGS. 2A and B. The method illustrated in FIGS. 2A and B is identical to that shown in FIGS. 1A and B with the exception that the capture of the nucleic acid analyte is effected by hybridization of the analyte to an immobilized capture nucleic acid located in the capture zone. As shown beginning in FIG. 2A and moving through 2B, the assay device comprises a test strip (A) containing an application zone which receives a liquid sample containing nucleic acid analytes (B1). The nucleic acid analyte (B1) (single-stranded) contains a reactive ligand (a). The test strip (A) contains a conjugate reporter (C) which is comprised of a reporter molecule (c) and a member of an immunoreactive or affinity reactive binding pair, (d). The binding pair member (d) is designed to react specifically with the reactive ligand (a) incorporated in the nucleic acid analyte. The reporter molecule (c) is similar to that discussed above. The test strip (A) further contains an immobilized capture nucleic acid (D1), irreversibly affixed to the bibulous material and located in the capture zone. The capture nucleic acid (D1) contains a sequence complementary to a portion of the analyte (B1) and is designed to hybridize to the analyte (B1) at that portion. When the test sample, containing the nucleic acid analyte (B1) is applied to the application zone the sample is moved down the test strip (A) by capillary action over the conjugate reporter (C) in the direction of the capture zone. As the nucleic acid analyte (B1) contacts the conjugate reporter (C), it is bound by the interaction of the reactive ligand (a) and the binding pair member (d) forming an analyte reporter complex (E1). Upon reaching the capture zone the analyte reporter complex (E1) hybridizes with the capture nucleic acid (D1) and is immobilized forming an immobilized hybrid analyte reporter complex (F1). Continued movement of the sample fluid draws excess reagents and unbound analyte past the capture zone. In the case where the reporter molecule (c) is an enzyme, substrate is added to the test strip (A) at the application zone after the excess reagents have moved past the capture zone. Reaction of the substrate with the enzyme results in detectable signal.

It will be recognized that the sequence of events outlined in FIGS. 2A and B may be altered without affecting the detection of the nucleic acid analyte. For example, it would be possible to effect the hybridization of the nucleic acid analyte (B1) to the capture reagent (D1) prior to the addition of the reporter conjugate (C). One of skill in the art will recognize that other variations of this embodiment are possible and are included within the scope of the present invention.

Figure 3A:
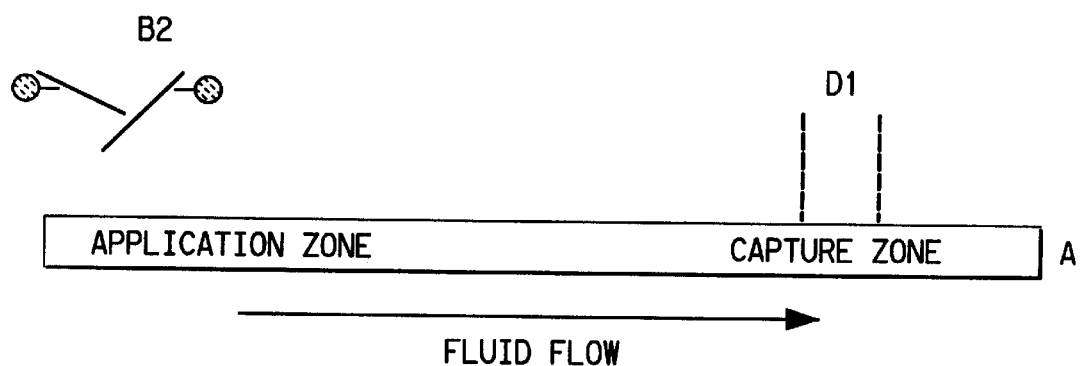

A third embodiment of the invention is outlined in FIGS. 3A and B. This embodiment relies on the incorporation of the reporter molecule into the nucleic acid analyte and the subsequent capture and detection by hybridization to an immobilized capture nucleic acid.

Beginning in FIG. 3A and moving through 3B, the assay device comprises a test strip (A) containing an application zone which receives a liquid sample containing nucleic acid analytes (B2). The nucleic acid analyte (B2) contains a reporter molecule (f) which has been incorporated into the terminal portions or the backbone of the analyte. The reporter molecule may be any signal producing moiety. However, it is most typically a fluorescent molecule or combination of molecules. In this embodiment no reporter conjugate is required since the reporter has been incorporated directly into the nucleic acid analyte. The test strip (A) further contains an immobilized capture nucleic acid (D1), irreversibly affixed to the bibulous material and located in the capture zone. The capture nucleic acid (D1) contains a sequence complementary to a portion of the analyte (B2) and is designed to hybridize to the analyte (B2) at that portion. When the test sample, containing the nucleic acid analyte (B2) is applied to the application zone the sample is moved down the test strip (A) by capillary action in the direction of the capture zone. Upon reaching the capture zone the nucleic acid analyte (B2) hybridizes with the capture nucleic acid (D1) and is immobilized forming an immobilized hybrid analyte reporter complex (F3). Continued movement of the sample fluid draws excess reagents and unbound analyte past the capture zone.

Figure 10B:
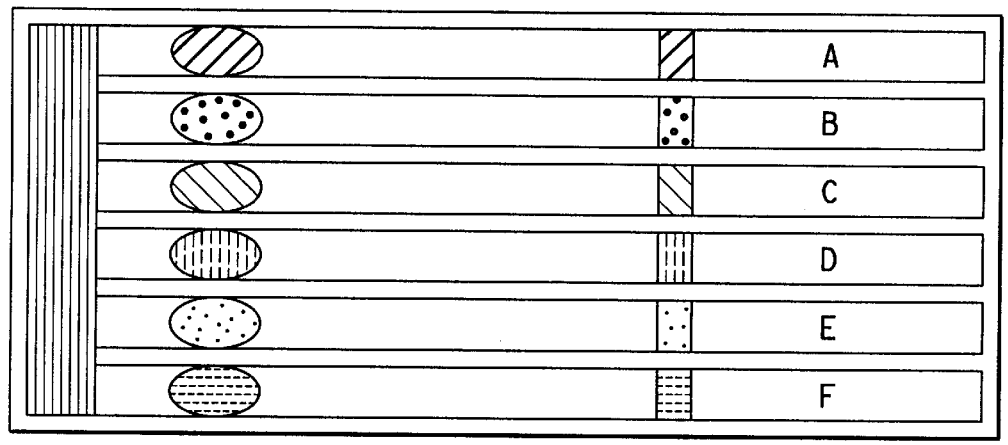

The present method is adaptable for the detection of multiple analytes on a single membrane. This may be accomplished in one of two formats as illustrated in FIGS. 10A and B. The simplest format would allow for the division of the test strip into separate lanes (FIG. 10B) where separate capture zones would be located for the capture and detection of individual analytes. Additionally, it is possible to perform the instant method where individual analytes may be detected from a single solution. For example, multiple capture moieties could be immobilized on the same membrane but at different capture zones as illustrated in FIG. 10A. Each capture moiety would possess specificity for a specific analyte, either by means of a unique ligand and reporter conjugate association or as the result of specific nucleotide base pairing. In one preferred embodiment the capture moiety could be a capture nucleic acid immobilized on the membrane at specific capture zones. Analytes contained in a single test would traverse the membrane and specifically hybridize with a single specific capture nucleic acid. In this format detection could be based on single or multiple reporter conjugates as illustrated in Example 5.

It will be readily apparent to one of skill in the art that the embodiments illustrated above represent only a portion of the total workable variations of the present method and that any obvious variation of the instant method will fall within the scope of the invention.

Binding Pairs

The present invention provides various binding pairs useful for preparing reporter conjugates and capture reagents. Members of specific binding pairs suitable for use in practicing the invention can be of the immune or non-immune type. Immune specific binding pairs are exemplified by antigen/antibody systems or hapten/anti-hapten systems. The antibody member, whether polyclonal, monoclonal or an immunoreactive fragment thereof, of the binding pair can be produced by customary methods familiar to those skilled in the art. The terms "immunoreactive antibody fragment" or "immunoreactive fragment" refer to fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, Proteins A, G, and immunoglobulins, etc. Also included are non-immune binding pairs which form a covalent bond with each other: exemplary covalent binding pairs include sulfhydryl reactive groups such as maleimides and haloacetyl derivatives and amine reactive groups such as isothiocyanates, succinimidyl esters and sulfonyl halides, etc. M. N. Bobrow, et al., *J. Immunol. Methods,* 125, 279, (1989).

Capture Reagents and Nucleic Acids

Capture regents suitable for use in the present method include either members of immune or non-immune binding pairs as discussed above or capture nucleic acids. The capture reagents are irreversibly immobilized to the test strip by methods well known in the art (Sambrook et al., *Molecular Cloning*, Cold Spring Harbor Laboratory Press., Vol. 2, 9.34–9.37 (1989)) and serve to capture the nucleic acid reporter conjugate in the capture zone or the strip.

Capture nucleic acids will generally be immobilized on nitrocellulose by ultraviolet irradiation, baking, capillary transfer or vacuum transfer and will contain sequence complementary to a portion of the nucleic acid analyte. Examples of nucleic acid immobilization on nitrocellulose and other suitable supports are given in Kalachikov, S. M., et al., *Bioorg. Khim.*, 18, 52, (1992) and Nierzwicki-Bauer, et al., *Biotechiques*, 9, 472, (1990). Alternatively, capture nucleic acids may incorporate a reactive ligand and may be immobilized as a result of the interaction between the ligand and an immobilized member of a binding pair.

Capture nucleic acids may be from any source and of any length but will most preferably be synthetically generated and between 10 and 300 bases in length. Methods of generating synthetic oligonucleotides are common and well known in the art. (Ausbel et al., *Current Protocols in Molecular Biology*, Supplement 9, 2.11 (1990)).

Reporters and Reporter Conjugates

The function of the signal producing system is to produce a product which provides a detectable signal at the capture zone, related to the amount of analyte bound to the capture reagent. Typically the signal producing system will incorporate a reporter conjugate comprising an antibody or member of a binding pair conjugated to either a radioactive label, enzyme, particle or fluorescent moieties.

Enzymes suitable for use in a reporter conjugate include, but are not limited to, hydrolases, lyases, oxido-reductases, transferases, isomerases and ligases. Others are peroxidase, glucose oxidase, phosphatase, esterase and glycosidase. Specific examples include alkaline phosphatase, lipases, betagalactosidase, horseradish peroxidase and porcine liver esterase. A preferred reporter conjugate will comprise an enzyme coupled to an antibody. Preparation of such conjugates may be accomplished using methods well known to those skilled in the art (see D. G. Williams, *J. Immun. Methods*, 79, 261 (1984)). In embodiments where enzymes serve as reporters, the substrate/enzyme reaction forms a product which results in a detectable signal, typically a change in color. In many cases chromogenic substances are an additional requirement for the color reaction. Chromogenic reagents are chosen on the basis of the reporter enzyme used. Some typical enzyme/chromogen pairs include, but are not limited to, b-galactosidase with potassium ferrocyanide or potassium ferricyanide; horse-radish peroxidase with 3,3' diaminobenzidine (DAB); Glucose oxidase with NBT and alkaline phosphotase with NBT and 5-bromo-4-chloro-3-indolylphosphate-4-toluidine (BCIP). Methods for the use of chromatogenic substance with enzyme reactions are well known in the art and are fully described by Tijssen, P., *Practice and Theory of Enzyme Immunoassays in Laboratory Techniques in Biochemistry and Molecular Biology*, eds., R. H. Burton and P. H. Van Knippenberg, (1988)).

Alternatively, reporter conjugates may make use of radioactive or florescent labels as the reporting moiety. Typical radioactive labels may include, but are not limited to, $^{125}I$, $^{35}S$, $^{32}P$, and $^{33}P$. Similarly suitable fluorescent reporter molecules may include but are not limited to fluorescein, rhodamine, rhodoamine$_{600}$ R-phycoerythrin and Texas Red. Suitable particles include those of latex that are typically dyed, submicron and uniform.

Target Nucleic Acid

The target nucleic acid is the moiety ultimately detected by the present method. Targets may be isolated from various bacterial or viral pathogens, or may be the subject of diagnostic analysis for genetic disease. Target nucleic acids ultimately may be prepared from any source where the detection of that target or portions of that target are representative of the analysis to be done. Target nucleic acids are not generally detected directly but will require amplification by methods discussed below.

Specifically, the target nucleic acid sequence may vary in length from 20 to 5000 bases; most preferably (if the target is to be used for PCR amplification) it will range between 30 and 1000 bases. If the target is used for LCR amplification the target length will range between 100 and 500 bases. The target may be double stranded (ds), comprising a hybrid duplex of two complementary nucleic acid strands, or may be single stranded (ss). Double stranded targets do not require production of a complementary antisense strand to participate in logarithmic chain polymerization.

Amplification Methods

The present method provides for the amplification of a target nucleic acid to produce a nucleic acid analyte. A variety of nucleic acid amplification methods are known in the art including thermocycling methods such as polymerase chain reaction (PCR) as well as isothermal methods such as Ligase Chain Reaction (LCR) and Strand Displacement Amplification (SDA). Additional isothermal methods of RNA replication such as Q-β-replicase and RNA dependent polymerase are contemplated to be within the scope of the present invention. Further, variations on these and related amplification methods are also contemplated, as in methods involving random primer sequences such as the RAPD method (Random Amplified Polymorphic DNA) used to detect genetic polymorphisms.

Logarithmic nucleic acid replication technology such as PCR or LCR provides highly sensitive means for amplifying copies of a specific nucleic acid sequence. These technologies afford two very important capabilities. One is the specificity of the replication process. Information from a single sequence can be specifically replicated in the presence of samples containing complex mixtures of nucleic acids and high concentration of proteins. The second is the high sensitivity afforded by the process. Replications of target DNA on the order of >$10^6$ fold can be achieved by a temperature recycle process. Currently, pathogens can be detected in mixtures of unknown samples by sequence probes; however, the sensitivity approaches approximately only $10^3$ cells/mL. Logarithmic sequence replication of target DNA has now greatly extended probe test sensitivity enabling as few as 1 to 5 cells/100 mL to be detected, Bej et al., *App. Environ. Microbiol.*, 56,307 (1990).

When target replication is performed by PCR to produce a nucleic acid analyte two specific primers are used (see primers 1 and 2 below). Each primer specifically hybridizes with one of the two complementary strands of the target (or if the target is single stranded (ss) one of the primers is specific for the second strand after synthesis). Replication of the target requires that the 5' end of the primer which is complementary to the -sense target strand (primer #2), corresponds to a region of the + sense strand which is 5' to the 3' end of the + sense strand specific primer (#1). Additionally, the primers should not contain regions with sufficient complementarity to form primer-dimers. Within these constraints, the total length of the primers may range from shorter than, to longer than, the target.

```
                                    <------5'primer #1
+ sense 5'-XXXXXXXXXXXXXXXXXXXXXXXXXXXX-3'

- sense 3'-YYYYYYYYYYYYYYYYYYYYYYYYYYYY-5'
primer #2  5'------>
```

Primers may also contain sequences at their 5' ends that have no complement in the target (5' overhang or 5' mismatch).

```
                                    <-------5' Primer #1
+ sense 5'-XXXXXXXXXXXXXXXXXXXXXXXXXXXX-3'

5'------> primer #2
- sense 3'-YYYYYYYYYYYYYYYYYYYYYYYYYYYY-5'
```

(X,Y represent complementary bases.)

This 5' overhang or 5' mismatch can be used to incorporate functionalized bases (e.g., binding member derivitized bases) on the primers.

Typically, in PCR-type amplification techniques the primers have different sequences and are not complementary to each other. Depending on the desired test conditions, the sequences of the primers should be designed to provide for both efficient and faithful replication of the target nucleic acid. Some simple rules are useful in selection and design of the primers. Typically, primers should be 10 to 35 base pairs in length having a 50 to 60%, G+C composition. The calculated TmS for a given primer pair should be balanced. For this purpose, a 2° C. for A or T and 4° C. for G or C can be added together to estimate the Tm of the oligonucleotide. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Virginia). Depending on the selected conditions, melting temperatures (TmS) between 55° C. and 95° C. are suitable. In addition to the TmS, the complementarity at the 3' end of the primers is an important consideration. Generally, complementarity of primer pairs should be avoided, especially at the 3' ends. Also, consecutive runs of C's and G's (3 or more) at the 3' ends of the primers along with palindromic sequences should be avoided. Consideration should also be given to the concentration of primer molecules in the replication milieu. Primer concentrations between 0.01 and 1.0 μM are generally suitable, with concentrations of about 0.05 to 1.0 μM being optimal.

When the LCR is used for replication of a target double stranded nucleic acid, two sets of target-specific primers will be required. The members of one set of primers are complementary to adjacent sequences found on a given strand of the target, while the members of the second set are complementary to adjacent sequences on the opposite strand. In this way a set of adjacent primers is specific for each target strand. During the replication process the target nucleic acid is heated to denature the two target strands. The four complementary oligonucleotide primers comprising the two primer sets are then hydridized near their melting temperature to the separated target strands. A thermal-stable ligase will covalently attach the adjacent primers on each target strand. Only adjacent primers that are perfectly complementary to the target will be ligated together. In this way, the products from the first stage of ligation become targets for the next round of ligation. The products thus increase exponentially with continued cycles of target denaturation, primer hybridization and ligation steps.

The requirements for non-complementarity between primers, size, base composition and melt temperature requirements of the primers tend to be similar to those stated above for PCR replication. Generally, primers for LCR replication should be sufficiently long so that each will preferentially bind to its specific binding site on the target nucleic acid. To insure specificity of ligation, reactions can be carried out near the melting temperature (Tm) of the oligonucleotide primers. At higher temperatures single-base mismatch at the junction can form. This results not only in imperfect double helix but destabilizes hybridization of the mismatched oligonucleotides.

Strand Displacement Amplification offers an alternative to LCR for the isothermal amplification of nucleic acids and may be used to amplify either a single stranded or double stranded target using either single or double primers respectively. Materials necessary for strand displacement amplification include either one or two short primers containing a site for HincII digestion, an exonucleas deficient DNA polymerase, HincII restriction enzyme and the bases dGTP, dCTP, dTTP and deoxyadenosine 5'[α-thio]triphosphate (dATP[αS].

If the target to be amplified is single stranded a single primer is used which binds to the targets at their complementary 3' ends forming a duplex with a 5' overhang at each end. The 5' overhang of the primer stand contains a recognition sequence for the restriction enzyme HincII. An exonuclease deficient DNA polymerase I extends the ends of the duplex using dGTP, dCTP, TTP and dATP[αS], which produces a hemiphosphorothioate recognition site. HincII nicks the unprotected primer strand of the hemiphosphorothioate site leaving intact the modified complementary strand. The exo-polymerase extends the 3' end at the nick and displaces the downstream complement of the target strand. The polymerization/displacement step regenerates a nickable HincII recognition site. Nicking and polymerization/displacement steps cycle continuously producing single-stranded complements of the target strand.

If a double-stranded target is to be amplified then two primers are used each having regions complementary to only one of the stands in the target. After heat denaturation the single stranded target fragments bind to the respective primers which are present in excess. Both primers contain restriction enzyme recognition sequences located 5' to the target binding sequences. Each primer-target complex cycles through nicking and polymerization/displacement steps in the presence of a restriction enzyme, a DNA polymerase and the three dNTP's and one dNTP[αS] as discussed above. An indepth discussion of SDA methodology is given by Walker, et al., *Proc. Natl. Acad. Sci. U.S.A.*, 89, 392, (1992).

RAPD markers have been used to detect genetic polymorphisms by making use of primers consisting of randomly generated sequences for target amplification. It is contemplated that RAPD amplification methods may be used within the present assay system to amplify and identify target nucleic acids. As with the above methods targets to be amplified may either be single or double stranded and will require standard amplification buffers, dATP, dCTP, dGTP and dTTP and a thermostable DNA polymerase such as Taq. The nucelotide sequence of the primers are about 9 to 10 bases in length, between 50 and 80% G+C in composition and contain no palindromic sequences. A complete discussion of the RAPD method is given by Williams et al., *Nucl. Acids. Res.,* 18, 6531 (1990) and in U.S. Pat. No. 5,126,239.

In any of the replication protocols, the primers may contain bases labeled with reporter(s) or labeled with one member of a specific binding pair. In this way, primer incorporation during the replication process can be used as a preferred means of introducing reporters and affinity labels in the replicated nucleic acids.

Ligand Incorporation into Nucleic Acid Analyte

In another preferred embodiment, the sequences of the nucleic acid analyte are designed to incorporate a ligand. For the purposes of the present invention ligands of less than 2000 molecular weight are preferred and ligands with molecular weights of less than 1000 are most preferred.

Variability in the positional orientation and number of the incorporated ligands lends flexibility to the analyte design, allowing for increased assay sensitivity and optimized conjugate interaction with the nucleic acid analyte. It is contemplated that ligands can be incorporated into one or both strands of a duplex nucleic acid analyte. Positionally, ligands can be incorporated either at the 5' or 3' ends of the analyte or incorporated on internal bases within the nucleic acid sequence, but incorporation internally is generally preferred. It is understood that any number of ligands may be incorporated per analyte, however, where the object is to achieve maximum sensitivity of the assay, preferably 10–30% of a particular substituted nucleotide is effective.

The method of incorporation of the ligand into the nucleic acid sequences may be accomplished either by chemical or enzymatic means, or by direct incorporation of ligand labeled bases into the target sequence. In a preferred approach, ligand incorporated sequences are prepared using ligand labeled bases or primers during polymerase chain reaction. Ligand incorporation can be accomplished either through the incorporation of primers modified with ligand(s) or by using ligand labeled dNTPs. Ligand labeled primers can be prepared using standard oligonucleotide cyanoethyl phosphoramidite chemistry by substituting selected bases with ligand modified phosphoramidite bases during primer synthesis. Alternatively, if primers are prepared with modified bases containing a linkable molecular spacer, the ligands can be chemically linked to the spacer after primer synthesis. Another method would make use of ligand labeled dNTPs or amino modified dNTPs which can be incorporated into a target nucleic acid sequence during the amplification procedure.

There are several advantages to synthesis of ligand incorporated nucleic acid sequences by PCR. For example, where labeled primers are used, it is possible to control both the positioning and number of ligands within one or both strands of the target sequence by the appropriate placement of the ligand in the primers.

In a preferred embodiment nucleic acid analytes are labeled with digoxigenin and biotin via a modified PCR protocol. Protocols for the creation of digoxigenin and biotin incorporated DNA are common in the art (Lion et al., *Anal. Biochem,* 188, 335 (1990); Kerkhof, *Anal. Biochem,* 205, 359, (1992)).

In another embodiment it is contemplated that various reporter molecules may be incorporated into the nucleic acid analyte. Labeling of nucleic acids with a radioactive or fluorescent molecule is well known in the art. For example, nucleic acids may be labeled on their 5' end using T4 polynucleotide kinase and $^{32}$P labeled ATP. The T4 kinase specifically transfers the radiolable from the ATP to a 5'OH group of the nucleic acid. This method is particularly useful for the end-labeling of small DNA or RNA molecules. Alternatively, radioactive 3' end-labeling of nucleic acids may be accomplished using a terminal transferase enzyme and a variety of radiolabels such as $^{32}$P, $^{35}$S, $^{125}$I, or $^{33}$P all incorporated into dNTP's as donors. Methods for the radio-labeling of nucleic acids are well known in the art and are described fully in Sambrook et al., *Molecular Cloning,* Cold Spring Harbor Laboratory Press., Vol. 2, 9.34–9.37 (1989).

Fluorescent reporter molecules may be incorporated into the nucleic acid analyte using labeled primers or labeled bases to produce the correspondingly labeled signal generating nucleic acids. In a preferred embodiment, it is desired to position specific labeled bases in the sequence so as to enable energy transfer between fluorophores. Specifically, energy transfer between suitably labeled bases can be achieved if the distance between the excitation fluorophore (F1) and the emission fluorophore (F2) are within 12 bases (ca. 50 Å) in the helical duplex assemblage. Cardullo et al., *Proc. Natl. Acad. Sci. USA,* 85, 8790 (1988). A more preferred distance is between 5 to 12 bases. This can be achieved by designing the primer sequences so that one of the labeled bases (F1 and F2) is alternately incorporated in the signal nucleic acid at each turn of the helix. Alternatively, the base sequence of the primers can be designed so that F1 and F2 are incorporated into opposite strands of the signal nucleic acid. The position of labeled bases is controlled so that on strand hybridization, F1 and F2 are positioned within the duplex at a distance of <50 Å. More preferably, F1 and F2 will be positioned on the same side of duplex one turn apart. Thus, within the signal nucleic acid, both interchain and intrachain labeled bases can position the fluorophores within a distance suitable for energy transfer.

The requirements of fluorophores which participate in energy transfer are well documented (Morrison, *Anal. Biochem.,* 174, 101 (1988)). Generally, to achieve energy transfer it is also important to select the appropriate combination of fluorophores used for labeling the excitation (F1) and emission (F2) bases so that the emission spectrum of the excitation fluorophore (F1) overlaps with the adsorption or excitation spectrum of the excitation fluorophore (F2). For example, the following fluorophore combinations include commonly available suitable candidates for energy transfer:

| Excitation Fluorophore (F1) | Emission Fluorophore (F2) |
| --- | --- |
| Pyrenebutyrate | b-Phycocrythrin |
| Fluorescein | Texas Red |
| Lucifer Yellow | Rhodamine |
| Lucifer Yellow | Texas Red |
| Fluorescein | Rhodamine |
| Fluorescamine | Fluorescein |

Test Strip

The test strip is the medium on which the assay of instant invention takes place. The test strip is generally composed of a chromatographic, bibulous material and encompasses an application zone and a capture zone as described above.

The chromatographic, bibulous materials that comprise the test strip are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, crosslinked dextran, agarose, polyacrylate, etc.; either used by themselves or in conjunction with other materials; ceramic materials; glass and the like. For the purposes of the present invention the most preferred material is nitrocellulose.

As the present method contemplates the use of both affinity and immuno-reactive capture methods as well as nucleic acid hybridization it is advantageous to employ a material suitable for both modes of operation. By far the most commonly used matrix for immobilization of nucleic acids is a microporous nitrocellulose membrane. Alternatively, microporous nylon membranes may also be used where better mechanical strength is desired. Optionally, introduction of positive ionic groups such as quaternary ammonium ions into nylon and nitrocelluose membranes may be desired to improve their wetting proprieties.

The preferred membrane can be a single structure such as a sheet cut into strips or it can be particulate material bound to a support or solid surface such as found, for example, in thin-layer chromatography.

The size of the strip is dependent on several considerations including the volume of the test sample to be applied, the concentration of the reagents residing in the strip and the make-up of the test sample fluid. Thickness of the strips will usually be no greater than 20% of the width, preferably 1 to 10%, more preferably 2 to 5%.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The length of the strip will depend on the concentration of the analyte and practical considerations such as ease of handling and will be about 2 cm to 40 cm, usually about 4 cm to 25 cm, preferably about 6 to 20 cm but may be of any practical length. The structure of the strip can be varied widely and includes fine, medium fine, medium, medium coarse and coarse. In general, smaller pore size and finer material will provide slow capillary flow and efficient capture of binding members on the strip. Coarser, more porous materials provide faster flow, but the efficiency of capture is reduced. Selection of the porosity of the material depends on the rate of binding of the binding pair members for a given assay.

Binding of binding pair members to the membrane may be accomplished by well-known techniques, commonly available in the literature. See, for example, *Immobilized Enzymes*, Inchiro Chibata, Halsted Press, New York (1978) and Cuatrecasas, *J. Bio. Chem.*, 245: 3059 (1970).

The support for the membrane where a support is desired or necessary will normally be water-insoluble, non-porous, and rigid and usually will be of the same length and width as the strip but may be larger or smaller. A wide variety of organic and inorganic materials, both natural and synthetic, and combinations thereof, may be employed provided only that the support does not interfere with the capillary action of the strip, or non-specifically bind assay components, or interfere with the signal producing system. Illustrative polymers include polyethylene, polypropylene, poly(4-methylbutene), polystyrene, poly-methacrylate, poly (ethylene terephthalate), nylon, poly(vinyl butyrate), glass, ceramics, metals, and the like.

Preparation of the Test Strip

To prepare the test strip for an assay the necessary reagents are deposited on the strip and the strip is equilibrated with the appropriate buffers.

Buffers and solvents useful with the instant method are well known in the art and examples are described in by Weng et al. (U.S. Pat. No. 4,740,468). Typically the pH for the lateral flow running buffer will usually be in the range of 4–11, more usually 5–10, and preferably in the range of about 6–9. The pH is chosen to maintain a significant level of binding affinity of the binding pair members and optimal generation of signal by the signal producing system. Various buffers may be used to achieve the desired pH and maintain the pH during the assay. Illustrative buffers include borate, phosphate, carbonate, Tris, barbital and the like. The particular buffer employed is not critical, but in individual assays, one buffer may be preferred over another.

Substantially constant, temperatures are normally employed for carrying out the assay. The temperatures for the assay and production of a detectable signal will generally be in the range of about 4° C.–50° C., more usually in the range of about 10° C.–40° C., and frequently will be ambient temperatures, that is, about 15° C.–25° C.

The concentration, in the liquid sample, of analyte which may be assayed will generally vary from about 0.1 ng/mL to 100 ng/mL. Considerations, such as the concentration of the analyte of interest and the protocol will normally determine the concentration of the other reagents.

While the concentrations of many of the various reagents in the sample and reagent solutions will generally be determined by the concentration range of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

Both reversible and irreversible binding of reagents can be effected on the solid support using techniques well known to those skilled in the art. Weetall, *Immobilized Enzymes, Antigens, Antibodies and Peptides*, (1975) Marcell Dekker, Inc., New York.

Briefly, a solution of lateral flow running buffer and an appropriate concentration of either a capture reagent or a capture nucleic acid is deposited on the test strip before blocking and washing such that irreversible binding occurs between the capture materials and the test strip. After blocking and washing the membrane, a solution of lateral flow running buffer containing sucrose and an appropriate concentration of reporter conjugate is deposited onto the strip such that the conjugate binds reversibly with the bibulous porous, chromatographic material (typically nitrocellulose; see Example 1, Membrane Preparation).

Where a capture nucleic acid is used the preferred material for the test strip is nitrocellulose. Immobilization of the capture nucleic acid may be accomplished by using high salt to adsorb the polynucleotides to its surface and baking at around 80° C. to permanently fix the adsorbed DNA or RNA. Alternatively, the nucleic acid may be fixed to the membrane by vacuum transfer in the presence of eqimoloar concentration of sodium chloride and sodium citrate, or by the use of ultraviolet irradiation (Nierzwicki-Bauer et al., *Biotechiques*, 9, 472, (1990).

Use of a capture nucleic acid requires the assay to be run under conditions amenable to nucleic acid hybridization. Hybridization typically takes place in a Ficoll buffer optionally containing polyvinylpyrrolidine, BSA, yeast tRNA, non-specific DNA, dextran sulfate, DTT and formamide. Hybridization may be accomplished either in solution or in solid phase where one member of the nucleic acid hybrid pair is immobilized on the test strip, in the capture zone. If solid phase hybridization is employed, the nucleic acid is immobilized to the membrane either by vacuum transfer or by exposure to UV light. Optionally a nucleic acid strand may be immobilized through the interaction of an incorporated reactive ligand with a member of a binding pair which is itself affixed to the membrane in the capture zone.

Solid phase nucleic acid hybridization will occur when the hybrid pairs are allowed to come in contact in hybridizing buffer at concentrations of about 5–25 ng/mL, for periods ranging from 10 min to 1 h, at room temperature. Hybridization in solution is typically done at higher temperatures to speed the reaction where the nucleic acid is denatured for 5 min at 94° C. followed by hybridization for 10 min at 55° C. Hybridization typically takes place in a buffer containing Tris, NaCl, $MgCl_2$ and $ZnCl_2$. Hybridizing DNA is reacted for about 15 min at room temperature and then washed free of unreacted components with wash buffer. Methods for nucleic acid hybridization are well known the art and several examples may be found in Sambrook et al., *Molecular Cloning*, Cold Spring Harbor Laboratory Press., Vol. 2, 9.34–9.37 (1989).

The following examples are meant to illustrate key embodiments of the invention but should not be construed to be limiting in any way. The abbreviations used have the following meanings: "sec" means second(s), "min" means minute(s), "h" means hour(s), "d" means day(s), "cm" means centimeter, "nm" means nanometer, "mL" means milliliter, "g" means gram, "BP" means base pair(s), "mol" means mole(s), "M" means molar, "C" means Centigrade scale, and "F" means Fahrenheit scale.

EXAMPLES

General Methods

Suitable methods of genetic engineering used herein are described in Sambrook et al., Molecular Cloning: A Laboratory Manual—volumes 1, 2, 3 (Cold Spring Harbor Laboratory: Cold Spring Harbor, N.Y., 1989) and in the instructions accompanying commercially available kits for genetic engineering. Digoxigenin, Biotin, avidin, 5-bromo-4-chloro-3-indolylphosphate-4-toluidine salt (BCIP), nitro-blue tetrazolium (NBT) as well as styreptavidn linked alkaline phosphatase and anti-digoxigenin linked alkaline phosphatase were obtained from Boheringer-Manheim, (Indianapolis, Ind.). Biotinylated dUTP (bio-dUTP), biotin-14-dATP and digoxigenin-11-dUTP were obtained from Bethesda Research Laboratories, Inc., Maryland. Unless otherwise specified all other standard reagents and solutions used in the following examples were supplied by Sigma Chemical Co. (St. Louis, Mo.).

Composition of Buffers and Wash Reagents

| Lateral flow buffer composition | Blocking buffer composition | Wash buffer composition |
|---|---|---|
| 10 mM Tris pH 8.0 | 10 mM Tris pH 8.0 | 10 mM Tris pH 8.0 |
| 150 mM NaCl | 2% BSA | 0.1% TRITON-X100 |
| 1 mM $MgCl_2$ | | 0.5% trehalose |
| 0.1 mM $ZnCl_2$ | | |
| 0.5% BSA | | |
| 0.1% TRITON-X100 | | |

Nucleic Acid Replication Composition

The replication composition useful in amplifying the target sequence in polymerase-type amplifications comprises a solution containing replication buffer that may optionally contain one or more labelled deoxynucleotides (dNTPs) as outlined below:

| PCR replication buffers |
|---|
| 1) Biotin labelling PCR |
|     10 mM Tris-HCl (pH 8.3) (@ 25° C.) |
|     50 mM KCl |
|     1.5 mM $MgCl_2$ |
|     0.001% (w/v) gelatin |
|     180 $\mu$M dATP |
|     200 $\mu$M dCTP |
|     200 $\mu$M dGTP |
|     200 $\mu$M dTTP |
|     20 $\mu$M biotin-14-dATP |
|     1 $\mu$M each primer |
|     1–10 ng test DNA |
|     25 units/mL Amplitaq ® DNA polymerase |
| 2) Digoxigenin labeling PCR |
|     10 mM Tris-HCl (ph 8.3) (@ 25° C.) |
|     50 mM KCl |
|     1.5 mM $MgCl_2$ |
|     0.001% (w/v) gelatin |
|     200 $\mu$M dATP |
|     200 $\mu$M dCTP |
|     200 $\mu$M dGTP |
|     180 $\mu$M dTTP |
|     20 $\mu$M digoxigenin-11-dUTP |
|     1 $\mu$M each primer |
|     1–10 ng test DNA |
|     25 units/mL Amplitaq ® DNA polymerase |
| 3) Biotin and digoxigenin labelling PCR: |
|     10 mM Tris-HCl (pH 8.3) (at 25° C.) |
|     50 mM KCl |
|     1.5 mM $MgCl_2$ |
|     0.001% (w/v) gelatin |
|     180 $\mu$M dATP |
|     200 $\mu$M dCTP |
|     200 $\mu$M dGTP |
|     180 $\mu$M dTTP |
|     20 $\mu$M biotin-14-dATP |
|     20 $\mu$M digoxigenin-11-dUTP |
|     1 $\mu$M each primer |
|     1–10 ng test DNA |
|     25 units/mL Amplitaq ® DNA polymerase |

Nucleic Acid Amplification

Target sequence replication may be performed using a DNA Thermal Cycler and Gene Amp Kit using recombinant Taq polymerase (Perkin-Elmer Cetus Corp., Norwalk, Conn.).

For amplification, 50 to 100 $\mu$L of the above replication composition is overlaid with 50 $\mu$L of mineral oil. The PCR reactions parameters are outlined below:

| PCR reaction parameters |
| --- |
| 1 min @ 94° C.<br>1 min @ 55° C.<br>1 min @ 72° C.<br>max ramping<br>40 cycles |

Solution Phase Nucleic Acid Hybridization Buffer

Solution phase nucleic acid hybridization takes place in buffer of the following composition:

10 mM Tris-HCl pH 8.0 (@ 25° C.)
150 mM NaCl
1 mM $MgCl_2$

Example 1

Detection of Amplified B. subtilis DNA Analyte

Example 1 illustrates the detection of amplified B. subtilis DNA by a lateral flow detection method.

Total DNA was isolated from target bacteria Bacillus subtilis strain BR151 (Bacillus Genetic Stock Center, Columbus, Ohio) by standard procedures as described in Sambrook et al., supra. The aprE gene of B. subtilis was selected as a target for amplification as it is distinctive of the host bacteria.

A specific segment of the aprE gene target DNA sequence (shown below) was amplified according to a modified polymerase chain reaction (PCR) protocol described above using primers 3 [SEQ ID NO.:2] and 4 [SEQ ID NO.:3] shown below:

processed identically in parallel. Following PCR, the sample was ethanol precipitated and resuspended in lateral flow buffer.

Membrane Preparation

A test strip consisting of a piece of nitrocellulose membrane (Schleicher & Schull, Keene, NH>5 micron, CAT #AE98) was prepared for assay.

First, avidin (1 µL of 0.5 mg/mL solution in lateral flow running buffer) was irreversibly deposited near the efferent end (capture zone) of the membrane. The membrane was then blocked for 1 h at room temperature with rocking in blocking buffer, washed 3× for 15 min at room temperature with rocking in wash buffer and soaked in 3.4 mg/mL NBT (Boheringer-Manheim, Indianapolis, Ind.) at room temperature with rocking for 5 min. Next, a conjugate (0.01 unit in 1.5 µL) composed of anti-digoxigenin coupled to alkaline phosphatase was reversibly deposited near the afferent end (application zone) of the membrane in lateral flow running buffer supplemented with 15% sucrose. Membranes were air dried and stored desiccated at room temperature until use.

Amplified aprE DNA Capture and Detection

Figure 4:
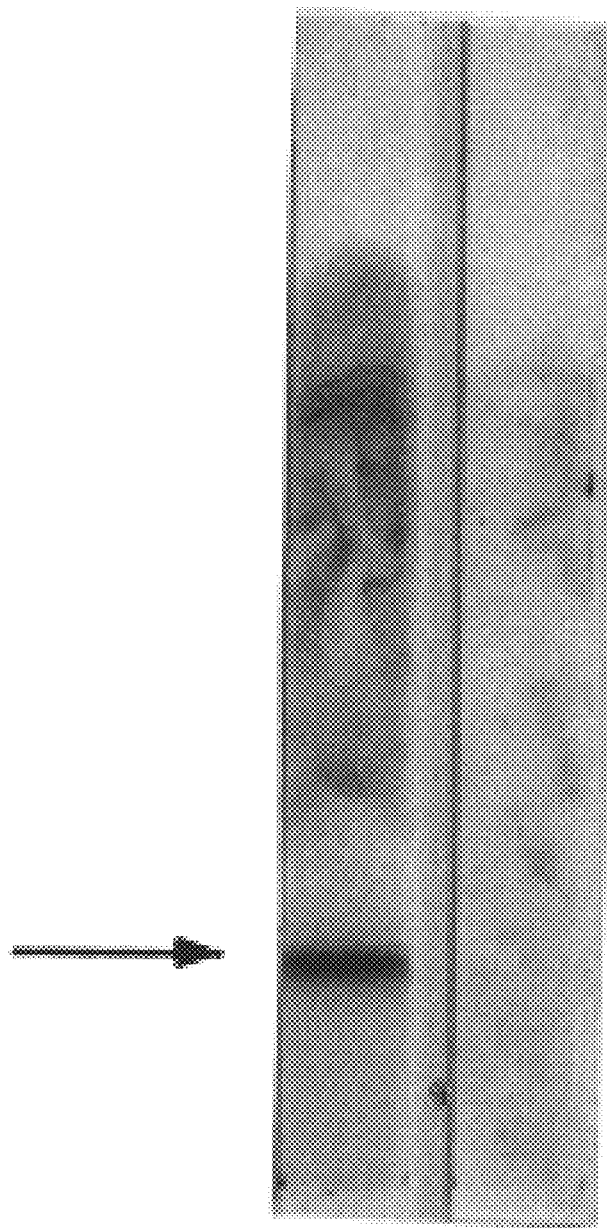
FIG. 4 is a photographic representation of the positive detection of aprE bacterial DNA by a lateral flow nucleic acid analyte detection system.

100–150 µL of a test solution consisting of 1–10 ng/mL amplified aprE target DNA in lateral flow buffer was applied to the application zone of the prepared nitrocellulose test strip. The control sample (which does not contain amplified target DNA) was also applied to a different, similarly prepared membrane. The solution was aloud to wick laterally across the membrane for 5–8 min. Next 100–150 µL of a solution of 5-bromo-4-chloro-3-indolyl phosphate-4-toluidine salt (BCIP) (0.018 mg/mL, pH 9.0) is wicked in the same fashion. After 20 min test results illustrated in FIG. 4 show a positive colorimetric result at the capture zone (arrow) of strip 1 where the aprE DNA amplified analyte was applied. Strip 2, where the control sample was applied, shows no calorimetric reaction in the capture zone.

B. subtilis aprE target:

```
  1 GATCCGAGCG TTGCATATGT GGAAGAAGAT CATATTGCAC ATGAATATGC [SEQ ID NO:1]

51 GCAATCTGTT CCTTATGGCA TTTCTCAAAT TAAAGCGCCG GCTCTTCACT

101 CTCAAGGCTA CACAGGCTCT AACGTAAAAG TAGCTGTTAT CGACAGCGGA

151 ATTGACTCTT CTCATCCTGA CTTAAACGTC AGAGGCGGAG CAAGCTTCGT

201 TCCTTCTGAA ACAAACCCAT ACCAGGACGG CAGTTCTCAC GGTACGCATG

251 TCGCCGGTAC GATTGCCGCT CTTAATAACT CAATCGGTGT TCTGGGCGTA

301 GCGCCAAGCG CATCATTATA TGCAGTAAAA GTGCTTGATT CAACAGGAAG

351 CGGCCAATAT AG
```

PCR primers:

Primer 3 5'-GATCCGAGCGTTGCATATGTG-3'          [SEQ ID NO:2]

Primer 4 5'-CTATATTGGCCGCTTCCTGTTC-3'         [SEQ ID NO:3]

Primer 3 consists of 21 bases and primer 4 contains 22 bases. Both primers were synthesized using an Applied Biosystem Synthesizer Model No. 392. Biotin and digoxigenin labeled nucleic acid analyte was prepared by amplifying the target DNA with both primers in the presence of 20 µM biotin-14-dATP and 20 µM digoxigenin-11-dUTP (PCR replication buffer #3 above). Amplification of the aprE DNA was carried out using the PCR parameters described above. A control sample which does not have the aprE target was Example 2

Lateral Flow Detection of PCR Amplified DNA through Hybridization to Complementary Capture Nucleic Acids Example 2 demonstrates three embodiments of solid phase hybridization in a lateral flow format used to detect amplified DNA. In the first embodiment a single-stranded complementary oligonucleotide (45 bases) was used as the capture reagent immobilized on the membrane to detect PCR-amplified, ligand-labeled DNA. In the second embodiment denatured double-stranded PCR-amplified DNA (182 BP) was used as a capture reagent and detected with hybridization by a single stranded nucleic acid reporter conjugate. In the third embodiment denatured double-stranded PCR-amplified DNA was used as a capture reagent to hybridize to double-stranded reporter labeled nucleic acid analyte.

Preparation of the Double-Stranded Nucleic Acid by DNA Amplification

The heat inducible promoter for *Escherichia coli* (*E. coli*) dnak operon (Cowing et al., Proc. Natl. Acad. Sci. U.S.A. 2679–2683 (1985)), 182 base pairs in length double stranded, was amplified by standard procedures, using the dnak primers 5 and 6 listed below. The DNA was either left unlabeled or labeled with Biotin-12-dUTP or digoxigenin-11-dUTP by methods described in Example 1 and the general methods.

The sequence of the *E. coli* dnak (182 base pairs double stranded) is given as follows:

```
AAAAGCACAA AAAATTTT                      [SEQ ID NO.:4]
TG CATCTCCCCC TTGATGACGT

GGTTTACGAC CCCATTTAGT AGTCAACCGC AGTGAGTGAG

TCTGCAAAAA AATGAAATTG GGCAGT-
TGAA ACCAGACGTT

TCGCCCCTAT TACAGACTCA CAACCA-
CATG ATGACCGAAT

ATATAGTGGA GACGTTTAGA TG
```

The underlined portions of the sequence indicate regions used to design a labeled oligonucleotide probe.

The 182 dnak promoter was amplified using the following primers:
Primer 5 5' GTT AGCCGGA TCC AAA AGC ACA AAA AAT 3' [SEQ ID NO.:5]
Primer 6 5' AGC AGT GAA TTC CAT CTA AAC GTC TCC A 3' [SEQ ID NO.:6]

A 5–20 ng aliquot of genomic DNA was amplified in a 100 μL reaction containing 0.4 μM primer, 10 mM tris-HCL pH 8.3, 50 mM KCl, 1.7 mM Mg Cl₂, 0.1 mM each dGTP, dATP, dTTP, dCTP and 2.5 Unit AMPLITAQ® DNA polymerase (Perkin Elmer/Cetus). The reaction solutions were overlaid with 50 μL of mineral oil. Amplifications were done in a Perkin Elmer Cetus DNA thermal cycler 480, using the following protocol: 35 cycles of 94° C. for 1 min, 50° C. for 1 min, and 72° C. for 2 min. Amplifications using these conditions typically produced 20 ng of DNA per μL. Primers 5 and 6 (25 base pairs in length) were designed and synthesized to produce an amplified DNA product of 207 base pairs.

Ligand Incorporation During PCR Amplification

Internal labelling of the dnak promoter was done with either Biotin-14-dATP or Dioxigenin-11-dUTP using the PCR replication buffers specified in the general methods and the conditions described above.

Preparation of the Single-Stranded Nucleic Acid Analyte Oligonucleotide

Synthetic oligonucleotides of 45 bases in length where synthesized to be used either as capture nucleic acids or as test analytes. The sequences of the oligonucleotides, referred to as primers 7 and 8 are given below:
Primer 7 (*E. coli* dnak promoter)
5' TGC ATC TCC CCC TTG ATG ACO TGG TTT ACG ACC CCA TTT AGT AGT 3' [SEQ ID NO.:7]
Primer 8 (*B. subtilis* aprE) 5' CGG CAG TTC TCA COG TAC GCA TOT CGC CGG TAC GAT TGC CGC TCT 3' [SEQ ID NO.:8]

Primers 7 [SEQ ID NO.:7] and 8 [SEQ ID NO.:8] were synthesized on an Applied Biosystem Synthesizer model #392. These sequences were also used as a specific reporters and labeled at the 5' ends with biotin during synthesis with a labeled phosphoramidite as described in Example 1 and in the general methods (Lion et al., Anal. Biochem, 188, 3335 (1990); Kerkof, Anal. Biochem, 205, 359. (1992)).

Buffers for Washing the Membranes Included

Wash Buffers:
Buffer A (100 mM Tris-HCl, 150 mM NaCl, pH 7.5)
Buffer B (100 mM Tris-HCl, 100 mM NaCl, and 50 mM MgCl₂ pH 9.0)
Buffer C is Buffer B with nitro-blue tetrazolium (NBT 0.34 mg per mL) and 5-bromo-4-chloro-3-indolyl-phosphate-4-toluidine salt (BCIP 0.018 mg per mL). NBT and BCIP were purchased from Boehringer Mannheim (Indianapolis, Ind.).

Detection Procedure

Following hybridization, 3% goat serum in Buffer A was used as a blocking reagent (Boheringer-Manheim, Indianapolis, Ind.). Detection of the digoxigenin-labeled analyte was observed with the addition of anti-digoxigeninalkaline phosphatase conjugate (1:1000 dilution in Buffer A, with 3% goat serum added. The membrane was washed twice in Buffer A and then once in Buffer B and then rocked for 3–5 min at room temperature in Buffer C (containing NBT and BCIP). In similar fashion, detection of the biotin-labeled analyte was observed with the addition of 1 μL of streptavidin 1:1000 dilution conjugated to alkaline phosphatase in phosphate buffered saline, pH 7.8. The membrane was washed twice in Buffer A and then once in Buffer B and then rocked for 3–5 min at room temperature in Buffer C (containing NBT and BCIP).

Lateral Flow Detection of PCR Amplified DNA by Hybridization to a Single-Stranded Nucleic Acid Capture Reagent For capture, one microliter of the unlabeled synthetic oligonucleotide, primer 7 [SEQ ID NO.:7] (0.035 μg) was spotted on the nitrocellulose membrane (Schleicher and Schuell, Keene, N. H., pore size >5.0 microns Cat# AE98). After spotting the nucleic acid was attached to the membrane at the capture zone with ultraviolet light for seven minutes on the Ultra.Lum UV transilluminator (Ultra-Lum Inc., Carson, Calif.).

Figure 3B:
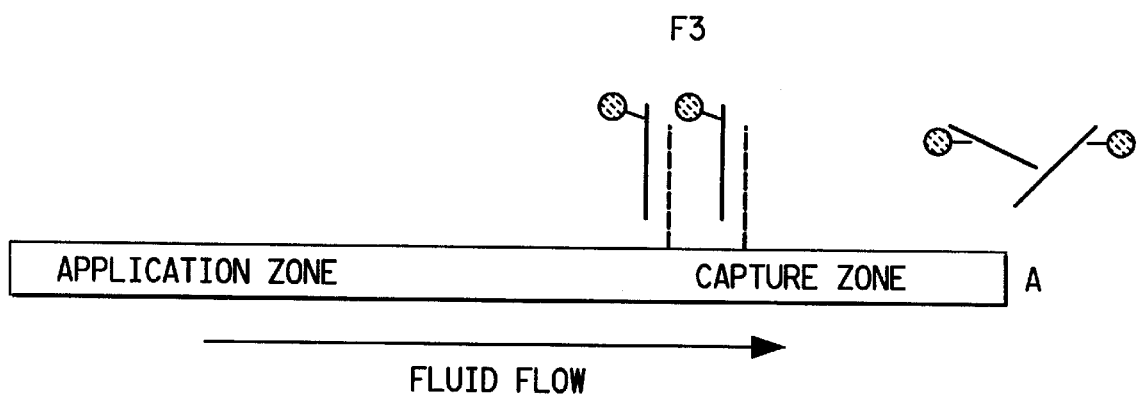
Figure 5:
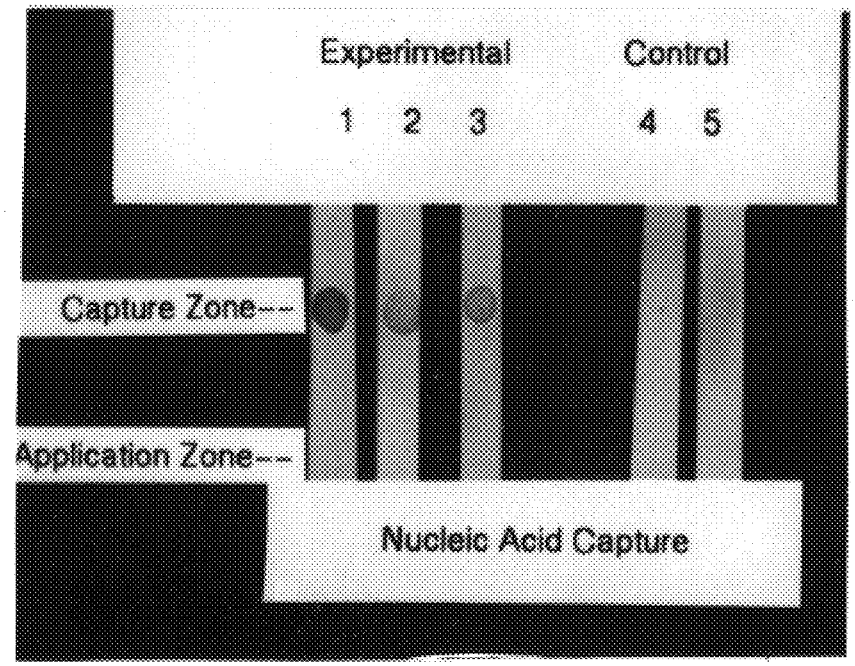
FIG. 5 is a photographic representation of the positive detection of dnak promoter DNA by a lateral flow nucleic acid analyte detection system, employing solid phase nucleic acid hybridization.

The denatured PCR amplified DNA analyte (dnak) (1–10 ng/ml) was labeled with either digoxigenin or biotin as described in above. The dnak analyte DNA was diluted in the 100 μL of lateral flow buffer (as described in general methods) and applied to a nitrocellulse test strip and was allowed to move by capillary migration on the membrane. The solution containing the DNA analyte was allowed to wick across the membrane for 5 min and hybridize to the capture nucleic acid at room temperature. Control DNA (*B. subtilis*, aprE promoter, Example 1) which was non-complementary to either the analyte or the capture nucleic acid and was labeled with either digoxigenin or biotin was also allowed to wick across the membrane strip with the synthetic capture reagent. The Detection Procedure described above was then used to obtain the colorometric reaction. FIG. 5, lanes 1 and 2, illustrate the colorimetric reaction indicating detection of the hybridized nucleic acid analyte. Lane 1 shows the biotin-labeled target and lane 2 the digoxigenin-labeled target. Negative lanes 4 and 5 in which non-complementary targets labeled with biotin (lane 4) and digoxigenin (lane 5) were wicked are additional confirmation of the results. This hybridization concept is illustrated in FIG. 3.

Lateral Flow Detection of a PCR Amplified DNA Product Through Hybridization to a Single Stranded Nucleic Acid Reporter Conjugate In this embodiment the double-stranded dnak PCR-amplified DNA was denatured by boiling at 95° C. for 5 min. One microliter of the DNA was immobilized on the membrane in the capture zone with UV light as described above. The single-stranded biotin-labeled complementary 45 base oligonucleotide (primer 7, SEQ ID NO.:7) was applied to the membrane and allowed to wick laterally into the capture zone, where hybridization with the PCR-amplified DNA occurred. Detection of the biotin-labeled oligonucleotide was accomplished with streptavidin conjugated to alkaline phosphatase according to the protocols described above.

FIG. 5, lane 3, demonstrates the detection of the PCR amplified dnak promoter hybridized with the biotin labeled oligonucleotide primer 7 using this format.

Lateral Flow Detection of a Double-Stranded PCR Product by Hybridization to a Denatured PCR Product The double-stranded PCR product (*E. coli* dnak promoter (207 bp)) was denatured by boiling vigorously at 95° C. for 5 min and then cooled by placing into ice. One microliter of the PCR product (20 ng/mL) was then spotted on the nitrocellulose membrane and illuminated and immobilized on the membrane with ultraviolet light as described above. The PCR analyte labeled with either biotin-or digoxigenin-was denatured by boiling the double stranded DNA vigorously at 95° C. for 5 minutes. The DNA analyte was diluted in the lateral flow buffer and allowed to move by capillary migration in the lateral flow format on the membrane. Control non-specific DNA target was also treated and applied in a manner similar to the experimental analyte. PCR analyte DNA took approximately 5 min to flow past the capture zone. Non-hybridized PCR analyte DNA was removed as the fluid flowed past the membrane. The Detection Procedure described above was then used to obtain the colorometric reaction.

FIG. 6, lane 1, demonstrates the hybridization and detection of biotin labeled PCR target and lane 2 demonstrates the detection of the digoxigenin labeled PCR target. Additional confirmation of the specificity of the data was observed from the lack of reaction product for the control non-specific targets labeled with biotin (lane 3) and digoxigenin (lane 4).

Example 3

Detection of a Bifunctional Nucleic Acid Analyte After Solution Phase Hybridization Example 3 illustrates the detection of amplified *B. subtilis* aprE DNA by the lateral flow detection method. In this example, target DNA amplified in the presence of biotin labeled dNTP was hybridized in solution with target DNA amplified in the presence of digoxigenin-labeled dNTP to demonstrate lateral flow detection of a bifunctional nucleic acid hybrid.

Total DNA was isolated from target bacteria *Bacillus subtilis* strain BR151 as described in Example 1 and the aprE gene was amplified using the same primers (3 and 4) and protocol described in Example 1. Two amplifications were carried out. Biotin-labeled nucleic acid was prepared by amplifying the target DNA with both primers in the presence of 20 μM biotin-14-dATP (PCR replication Buffer #1 above). Similarly, digoxigenin-labeled nucleic acid was prepared by amplifying the target in the presence of 20 μM digoxigenin-11-dUTP (PCR replication Buffer #2 above). Amplification of the aprE DNA was carried out using the PCR parameters described above.

Following PCR, samples were ethanol precipitated and resuspended in hybridization buffer.

Hybridization of Labeled Capture and Analyte DNA

For solution hybridization, the combined amplification products were denatured by heating for 5 min at 94° C. followed by hybridization for 10 min at 65° C. An amplified biotin-labeled non-aprE target was hybridized to digoxigenin-labeled aprE target in parallel as a control.

Membrane Preparation

Three test strips consisting of a piece of nitrocellulose membrane (Schleicher & Schull, Keene, NH >5 micron, CAT #AE98) was prepared for assay as described in Example 1.

Hybrid aprE DNA Capture and Detection

100–150 μL of a test solution consisting of 1–10 ng/mL hybridized DNA in lateral flow buffer was applied to the application zone of the prepared nitrocellulose test strip 2 (FIG. 7). In similar fashion, aprE target amplified DNA, labeled only with biotin, was applied to the application zone of test strip 1, and the control hybridization sample was applied to test strip 3. The solutions were allowed to wick laterally across the membranes for 5–8 min. Next 100–150 μL of a solution of 5-bromo-4-chloro-3-indolyl phosphate-4-toluidine salt (BCIP) (0.018 mg/mL, pH 9.0) is wicked in the same fashion. After 20 min test results illustrated in FIG. 7 indicated a positive result: a purple precipitate at the avidin deposited capture zone of test strip 2.

FIG. 7 shows the three test strips (1, 2 and 3) that have all been prepared in an identical fashion. Strip 1 was loaded with amplified aprE target DNA labeled only with biotin. Strip 2 was loaded with DNA from hybridization of biotin-labeled aprE target with digoxigenin-labeled aprE target. Strip 3 was loaded with DNA from hybridization of biotin-labeled non-aprE target and digoxigenin-labeled aprE target. As can be seen from the data, a positive result is obtained only when a bifunctionally-labeled nucleic acid analyte is generated by hybridization.

Example 4

Detection of RAPD Amplified Nucleic Acid Analytes for the Purpose of Identifying Genetic Polymorphisms This example demonstrates the feasibility of using the lateral flow method in combination with hybridization reactions using primers of arbitrary sequence to detect genetic polymorphisms. Here the target nucleic acid may be either single- or double-stranded and is amplified using RAPD primers in the presence of ligand labelled dNTP's to produce ligand labelled capture and analyte nucleic acids.

The following are particular variations of the process presented, although the claims are not limited to these variations of the method: (a) RAPD products are bound to the substrate (via biotin or otherwise) and then hybridized with a labelled (fluorescein or otherwise) detection probe; (b) RAPD products and the detection probe are hybridized together in solution and then the hybrid is bound to the substrate via the RAPD DNA (biotinylated); (c) RAPD products (fluorescein or otherwise labelled) and capture probe (biotinylated) are hybridized in solution and then the hybrid is bound to the substrate via a capture probe; (d) the capture probe is bound (via biotin or otherwise) to the substrate and then hybridized with the labelled (fluorescein or otherwise) RAPD. The capture and detection probes contain a binding moiety (biotin) or a detection moiety (fluorescein) depending on the probe's specific role.

Preparation of Capture Nucleic Acid 10-mer oligonucleotides (Operon Technologies, Alameda, Calif.) are used as primers in RAPD reactions (U.S. Pat. No. 5,126,239) with *B. napus* or soybean genomic DNA. A 5–20 ng aliquot of genomic DNA is amplified in a 25 μL reaction containing 0.4 μM primer, 10 mM Tris-HCl (pH 8.3) at 25° C., 50 mM KCl, 1.7 mM $MgCl_2$, 0.001% gelatin, 0.1 mM each dGTP, dATP, dTTP, dCTP and 1 unit AmpliTaq® DNA polymerase (Perkin-Elmer Cetus). The reactions are overlaid with 50 μL mineral oil and amplified in a Perkin-Elmer Cetus DNA thermal cycler using the following protocol: 40 cycles of 94° C. for 1 min, 35° C. for 1 min, and 72° C. for 2 min. Amplification in these conditions typically produces 20 ng DNA/μL.

Polymorphisms are identified by electrophoresis of the RAPD amplification products on 1.2% agarose gels containing ethidium bromide. The polymorphic bands contain DNA that may be used either as capture nucleic acids or as detection probes. This DNA is prepared as follows: Gel plugs containing polymorphic bands of interest are removed using 0.8 mm diameter glass capillaries. The agarose plugs are heated for 10 min at 80° C. in 100 μL 0.1 M Tris (pH 8). One μL aliquots of 1:10 and 1:100 dilutions of this solution are taken for re-amplification in RAPD conditions for twenty or thirty cycles of amplification. The purity of the re-amplified band is checked by agarose gel electrophoresis.

For use as either a capture nucleic acid or a detection probe, the band of interest is re-amplified in a larger volume (50–100 μL) using 5'-biotin or 5'-fluorescein-labeled primer (Operon Technologies, Alamdea, Calif.). Final purification of the re-amplified band is accomplished by means well known in the art, for example, by using the protocols and materials provided with WIZARD PCR DNA Purification System (Promega, Maidson, Wis). Re-amplifications may also be performed on cloned RAPD DNA.

FIG. 8 shows an electrophoretic separation of two lines of *B. napus* RAPD amplification products where two polymorphic bands are identified in lanes 3 and 9 (arrows). For the purposes of the present illustration the polymorphic band shown in lane 9 will be followed. The RAPD primer to be used for the amplification of *B. napus* DNA and for the production of the band seen in FIG. 8, lane 9 is as follows:

Primer 9 5'-GGAGTACTGG-3'[SEQ ID NO. :9]

In a similar fashion FIG. 9 shows an electrophoretic separation of genomic DNA from soybean and the identification of a polymorphic band (lane 6) using the following RAPD primer:

Primer 10 5'-GCGGTAGATG-3'[SEQ ID NO.:10]

As described above the polymorphic bands are excised from their respective gels and converted to capture or detection probe DNA by re-amplification in the presence of labeled primers. *B. napus* DNA excised from band 9 (FIG. 8) is re-amplified with the biotinylated primer:

Primer 11 5'-BCCAGTACTCC-3'[SEQ ID NO:11]

Soybean DNA excised from band 6 (FIG. 9A) is re-amplified with the fluoresceinated primer:

Primer 12 5'-FGCGGTAGATG-3'[SEQ ID NO.:12]
and the biotinylated primer:

Primer 13 5'-BGCGGTAGATG-3'[SEQ ID NO.:13]
and the results are shown in FIG. 9B, lanes 4 and 5 and 9B, lanes 2 and 3, respectively. ("B" and "F" at the 5' end of Primers 11, 12 and 13 signify biotin and fluorescein respectively.)

Preparation of Nucleic Acid Analyte

Target DNA (*B. napus* or soybean) is amplified with the appropriate biotinylated primer to yield RAPD amplification products containing the band of interest at a concentration of about 20 ng/μL, using the RAPD conditions described above for the capture nucleic acid. Genomic DNA from individuals negative for the band of interest is used with the same primer as a negative control. A small amount of the band of interest may be present in the "negative" individuals. Therefore, an additional negative control may be provided by samples amplified using a different RAPD primer. For single-label assays, a biotinylated primer is used in the amplification, and for double-label assays a fluoresceinated or biotinylated primer is used. For the purposes of this illustration appropriate primers for the amplification of the *B. napus* target will be primer 11 [SEQ ID NO.:11] and appropriate primers of the amplification of the soybean target will be primers 12 [SEQ ID NO.:12] or 13 [SEQ ID NO.:13].

Preparation of Conjugate Reporters

Alkaline phosphatase-linked anti-fluorescein antibody (DuPont NEN, MA, at a dilution of 1:1000 or Boehringer-Mannheim, at a dilution of 1:2500), a streptavidin-linked alkaline phosphatase (Amersham, at a final dilution of 1:5,000) are used as reporters for detection of fluorescein and biotin, respectively. Alkaline phosphatase is detected as described in Example 3 where alkaline phosphatase is detected with 5-bromo-4-chloro-3-indolyl phosphate-4-toluidine salt (BCIP) and nitro-blue tetrazolium (NBT). All color reagents are diluted according to manufacturer's specifications.

Horseradish peroxidase (HRP) conjugate may also used. For preparation of an HRP conjugate Pierce streptavidin-HRP diluted 1:10,000 is used with 3,3',5,5'-tetramethylbenzidine (TMB) and 2,2'-azino-di[3-ethylbenzthiazoline-6-sulfonic acid] (ABTS) substrates (BioRad, Hercules, Calif., absorption at 605 nm and 405 nm respectively).

Preferred Embodiments

It will be evident to the routineer that the use of primers of arbitrary sequence for the detection of genetic polymorphisms in the lateral flow format may be accomplished according to a variety of protocols. For example, a single ligand (typically biotin) could be used to label both the RAPD amplified target (analyte) from test and control samples, and the re-amplified polymorphic capture nucleic acid. In this embodiment the capture nucleic acid is first immobilized on the test strip in the capture zone where it is allowed to hybridize to the RAPD amplified analyte, after the free biotin binding sites of streptavidin have been blocked with a biotin buffer. This embodiment, although useful, is not preferred due to a relatively high background produced by small differences between the signals from the test vs. the control samples. RAPD amplified analyte DNA is derived from samples positive or negative for the polymorphic DNA and negative and control samples which contain little or no polymorphic DNA. The high background produced in the single label method is thought to arise from the presence of small amounts of polymorphic DNA in negative and control samples. If the capture probe is first immobilized and then allowed to hybridize with the RAPD amplified analyte, the small amount of polymorphic DNA present in the negative sample may be significant enough to saturate the capture nucleic acid leading to a poor signal to noise ratio in the assay.

To improve the assay sensitivity it is preferred that a double label method is used. In this preferred embodiment the RAPD amplified target (analyte) and the re-amplified polymorphic probe capture DNA are labelled with either biotin or fluorescein where the analyte and the capture are not labelled with the same ligand. Hence, a biotin labelled analyte is paired with fluoresceinated capture nucleic acid or visa versa. In this embodiment the RAPD amplified target (analyte) from test and control samples, containing a first ligand is immobilized on the test strip and subsequently allowed to hybridize with the detection probe containing a second and different ligand. The reporter moiety binds to the second ligand for detection. Ordering the assay in this fashion allows for proportional detection of the polymorphic DNA in the test sample and the control and results in a higher signal to noise ratio in the assay. What follows is a description of the operation of the preferred double label embodiment and the less preferred single label embodiment.

Hybridization and Detection of Fluoresceinated Analyte; Double Label Method

The RAPD amplified analyte may be fluoresceinated as described above, and hybridized with a biotinylated capture nucleic acid.

A test strip consisting of a piece of nitrocellulose membrane was prepared for assay essentially as described in Example 3 where avidin (1 µL of 0.5 mg/mL solution in lateral flow running buffer) is irreversibly deposited near the efferent end (capture zone) of the membrane.

Biotinylated soybean capture nucleic acid is applied to the membrane as described above. The membrane is then washed 2× in 0.5M SSC for 15 min each. Next denatured soybean RAPD amplified nucleic acid analyte, fluoresceinated at the 5' end is diluted to 20 ng/mL and applied to the nitrocellulose test strip for hybridization to the capture DNA. The hybridization reaction is allowed to proceed for 20 min at room temperature. Following hybridization the test strip is rinsed twice in 0.5M SSC for 15 min each.

Detection of the hybridized fluoresceinated detection probe was observed with the addition of 1 µL of anti-fluorescein 1:1000 dilution conjugated to alkaline phosphatase in phosphate buffered saline, pH 7.8. The membrane is washed twice in buffer A (Example 2) and then once in buffer B (Example 2) and then incubated at room temperature with nitro-blue tetrazolium (NBT) (3.4 mg/mL) and BCIP (0.018 mg/mL) while rocking for 30 min. After 20 min test results are read; a positive result indicated by a purple precipitate at the avidin deposited capture zone of test strip.

Hybridization and Detection of Biotinylated Analyte: Single Label Method

A test strip consisting of a piece of nitrocellulose membrane was prepared for assay essentially as described above. 100–150 µl of a test solution consisting of 1–10 ng/mL biotinylated B. napus capture DNA in hybridizing buffer is applied to the application zone of the prepared nitrocellulose test strip. The solution is allowed to wick laterally across the membrane for 5–8 min. The membrane is then washed 2× in 0.5M SSC containing biotin (25 mg/100 mL) for 15 min each. Next denatured (90° C., 10 min) B. napus RAPD amplified nucleic acid analyte, biotinylated at the 5' end is diluted to 20 ng/mL and applied to the nitrocellulose test strip for hybridization to the capture DNA. The hybridization reaction is allowed to proceed for 30 min at room temperature. Following hybridization the test strip is rinsed twice in 0.5M SSC containing biotin (25 mg/100 mL) for 15 min each, followed by a final wash in 0.5M SSC minus biotin.

Detection of the hybridized biotinylated analyte was observed with the addition of 1 µL of streptavidin 1:1000 dilution conjugated to alkaline phosphatase in phosphate buffered saline, pH 7.8. The membrane is washed twice in buffer A (Example 2) and then once in buffer B (Example 2) and then incubated at room temperature with nitro-blue tetrazolium (NBT) (3.4 mg/mL) and BCIP (0.018 mg/mL) while rocking for 30 min. After 20 min test results are read where a positive result is indicated by a purple precipitate at the avidin deposited capture zone of test strip.

EXAMPLE 5

Multi-Analyte Detection

The hybridization format is used to detect several PCR amplified targets on the same membrane (FIG. 10). Two oligonucleotide capture reagents (45 bases in length; Primers 7 and 8) are immobilized on the membrane 1 cm apart using UV light as described above. Each oligonucleotide sequence is a specific complement to one of two target DNA's. The first PCR DNA analyte, E. coli dnak promoter (SEQ ID NO.:4, Example 2) is amplified using primer 5 (SEQ ID NO.:5) and primer 6 (SEQ ID NO.:6) and labeled with biotin during the amplification as described in above. The second analyte, B-subtilis, aprE promoter, (SEQ ID NO.:1, Example 1) is labeled with biotin during amplification using the methods above, and primer 3 (SEQ ID NO.:2) and primer 4 (SEQ ID NO.:3). This mixture of target DNA's in 100 µL in running buffer (see general methods) are then allowed to wick across the membrane. The Detection Procedure described above is used to obtain the colorometric reaction.

On a single membrane two or more specific amplified DNA's can be observed as illustrated in FIG. 10A).

EXAMPLE 6

Detection of Double-Stranded DNA Without Hybridization Using Different Avidin Capture Reagents Example 6 demonstrates:
(i) detection of double stranded nucleic acid analytes in a lateral flow method; and
(ii) detection of multiple nucleic acid analytes in a pooled sample by solid phase hybridization in the lateral flow format.

Membrane Preparation

Nitrocellulose membranes were prepared by irreversibly depositing 1 ul of 2 mg/ml solutions of Avidin (Zymed San Francisco) or ExtrAvidin® (Sigma, St. Louis, Mo.) and Streptavidin (Zymed, San Francisco, Calif.).

Amplification and Labelling

A 99 base fragment target DNA (1) (listed below) was amplified with oligonucleotide primers p1 and p2 using PCR conditions as described in Example 1.

99 mer Base Target DNA (1)

5' GCTTCAGCGC CACATACATC ATACAGCACC ACAGACCACG CAACTCTAGA GGATCCCGGG TACTGTTTGT CTTCCTGCCT TTGCTGATGC CGCTTCTGC 3' [SEQ ID NO:14]

p1
GCTTCAGCGCCACATACATCAT [SEQ ID NO:15]

p2
GCAGAAGCGGCATCAGCAAA [SEQ ID NO:16]

Target amplification and ligand incorporation was accomplished using PCR protocols in the presence of 10% biotin-14-dATP and 10% digoxigenin-11-dUTP.

Lateral Flow Method

All reactions were carried out at room temperature. The undenatured (double-stranded) PCR product (1 ul) labeled with both biotin and digoxigenin was diluted into 19 ul of lateral flow buffer (GENERAL METHODS) containing 0.5% BSA. The diluted PCR product was spotted on the membrane and allowed to migrate through the strip and contact the capture zones; XA, SA, AV, for 5 minutes. (FIG. 11) Control strips contained PCR product labeled only with biotin. After chromatographic migration, the membranes were placed for 10 minutes in 1–2 ml 30% goat serum diluted in Buffer A (100 mM tris base, 150 mM NaCl, pH 7.5). The membranes were then placed for 30 minutes in anti-digoxigenin-alkaline phosphatase (Boehringer-Mannheim) diluted 1:1000 in Buffer A containing 3% goat serum. The membranes were rinsed twice, for 5 minutes each, in Buffer A and then placed in Buffer B (100 mM tris base, 100 mM NaCl and 50 mM $MgCl_2$, pH 9.5) for 2 minutes. The membranes were then placed in the chromogenic solution substrate solution (NBT/BCIP) from Moss Inc, Pasadena, Calif. and allowed to develop for 5 minutes until the color developed. Data is presented in FIG. 11.

FIG. 11 shows the capture and detection of ligand labeled, double-stranded, PCR product on nitrocellulose membranes after chromatographic migration of the diluted DNA. Membrane strip A compares the capture and detection of double-stranded DNA by ExtrAvidin® (XA), Streptavidin (SA) and Avidin (AV). Membrane strip B shows the capture zone printed as a line and in the shape of a "B". As expected the control membrane strip, printed as with membrane B, fails to detect the PCR product labeled only with biotin. The arrow indicates the direction of flow of the PCR product for all membrane strips.

EXAMPLE 7

Multiple Specific DNA Detection by Rapid— Hybridization Capture

This Example demonstrates the detection of three different target DNA's by specific probe capture.
Membrane Preparation Three single-stranded probes ranging in size from 45–57 nucleotides in length were irreversibly immobilized to nitrocellulose membranes at three capture zones using ultraviolet irradiation of 1.5 Joules/$cm^2$.

The single stranded probe, p3, (complementary to the apr target DNA (2)) was immobilized on Capture Zone 1. The single stranded probe p4 (complementary to the *E. coli* dnaK target DNA (3)) was immobilized in Capture zone 2. The single stranded probe p5 (complementary to the 99 base target DNA (1) shown above in experiment 1) was immobilized in Capture zone 3. p3–p5 and their respective target DNA sequences are shown below. The theoretical melting temperatures (tm) of all three probes ranged from 70–80° C. under the lateral flow buffer conditions.
p3
CGG CAG TTC TCA CGG TAC GCA TGT AGC CGG TAC GAT TOGC CC TCT [SEQ ID NO:17]
*B. subtilis* apr target DNA (2)
1 GATCCGAGCG TTGCATATGT GGAAGAAGAT CATATTGCAC ATGAATATGC
51 GCAATCTGTT CCTTATGGCA TTTCTCAAAT TAAAGCGCCG OGCTCTTCACT
101 CTCAAGGCTA CACAGGCTCT AACGTAAAAG TAGCTGTTAT CGACAGCGGA
151 ATTGACTCTT CTCATCCTGA CTTAAACGTC AGAGGCGGAG CAAGCTTCGT
201 TCCTTCTGAA ACAAACCCAT ACCAGGACGG CAGTTCTCAC GGTACGCATG
251 TGCCGGTAC GATTGCCGCT CTTAATAACT CAATCGGTGT TCTGGGCGTA
301 GCGCCAAGCG CATCATTATA TGCAGTAAAA GTGCTTGATT CAACAGGAAG
351 CGGCCAATAT AG [SEQ ID NO:18]
p4
TGC ATC TCC CCC TTG ATG ACG TGG TTT ACG ACC CCA TTT AGT AGT CAA CCG C [SEQ ID NO:19]

*E. coli* dnak target DNA (3)
1 AAAAGCACAA AAAATTTTTG CATCTCCCCC TTGATGACGT GGTTTACGAC
51 CCCATTTAGT AGTCAACCGC AGTGAGTGAG TCTGCAAAAA AATGAAATTG
101 GGCAGTTGAA ACCAGACGTT TCGCCCCTAT TACAGACTCA CAACCACATG
251 ATGACCGAAT ATATAGTGGA GACGTTTAGA TG [SEQ ID NO:20]
p5
ACA GCA CCA CAG ACC ACG CAA CTC TAG AGG ATC CCG GGT ACT GTT TGT CTT CCT GCC [SEQ ID NO:21]
99 mer base Target DNA (1)
5' GCTTCAGCGC CACATACATC ATACAGCACC ACA- GACCACG CAACTCTAGA GGATCCCGGG TACT- GTTTGT CTTCCTGCCT TTGCTGATGC CGCT- TCTGC 3'[SEQ ID NO:14]
Amplification PCR amplification was carried out on three target DNA's listed above in the presence of 10% digoxigenin- 11-dUTP, and conditions outlined in Example 1. PCR products were denatured by heating to 100° C. and rapidly immersing in ice. PCR amplification products were diluted to 1:20 in 100 ul of lateral flow buffer, spotted on the membrane and allowed to wick across the capture zone over a 5 minute period. Detection data is shown in FIG. 12.

Strip A (FIG. 12) contains PCR amplification products from amplification of all three targets. Strip B contains amplification products from the amplification of Targets (3) and (1). As can be seen by the data, amplification products from the targets (3) and (1) were specifically captured on capture zones 2 & 3 by their complementary probes but not by the probe on capture zone 1. Similarly strips C&D, containing amplification products from the amplification of Targets (2) and (3) respectively demonstrated hybridization only to the specific capture probes and not to the non-specific probe. In each of strips E, F, G containing amplification products from targets (1), (3) and (2) respectively, only a single analyte was detected.

After capture, the membranes were then soaked in 30% goat serum diluted in lateral flow buffer for 10 minutes. Next the membranes were placed in 1:1000 anti-digoxigenin alkaline phosphatase in 3% goat serum for 15 minutes. Membranes were rinsed twice in Buffer A for 2 minutes each and then rinsed in Buffer B for 2 minutes. The substrate chromogenic substance (NBT/BCIP) was used as previously described for 5 minutes.

The DNA targets did not hybridize non-specifically to other probes on the membrane but were specific for their complementary sequence. The capture of the specific targets occurred with the short hybridization interval of 5 minutes.

EXAMPLE 8

Detection Of Non-Denatured PCR Amplified DNA In The Lateral Flow Method

This experiment shows the detection of non-denatured PCR amplified DNA in the lateral flow format. PCR amplification was carried out under conditions as described previously using digoxigenin 11-dUTP (GENERAL METHODS and Example 2). PCR products can be stored at 4° C. for several months before either the denaturation or non-denaturation method. In the present experiment the PCR product was stored for two months before the lateral flow procedure. The target used for this example was from the Venezuelan equine encephalitis (VEE) (sequence from Kinney, *Virology*. 170, 19–30,(1989)). The example specifically, illustrates in the detection of the amplified fragment of the E2 glycoprotein of the VEE genome.

Primary amplifications of the VEE reverse transcriptase product with primers, VE1 156 and VE1862 (Table 1, [1]), resulted in a 707 bp product. Secondary amplifications were done with nested primers, (VE1281 and VE1569) which produced a 289 bp product. The membrane preparation and probe immobilization procedure were described in Example 2. Quantification was done using the Eagle Eye 11 Video System (Stratagene, La Jolla, Calif.) and the NIH Image Analysis program, Image 1.54.

For the denatured product, the lateral flow hybridization procedure was done as described above in Examples 6 and 7 and involved a 5 minute denaturation at 96° C. and quick cooling of the ligand labeled PCR product prior to running the PCR product on the membrane strips (FIG. 13, membrane A). FIG. 13 shows the detection of the VEE 289 bp PCR products, denatured (A) and non-denatured (B). The digoxigenin labeled product was either denatured or not denatured before running on the lateral flow membranes. Arrow indicates the non-denatured product at the specific capture zone containing the immobilized probe for the VEE 289 fragment. Surprisingly, for the non-denatured product (FIG. 13 membrane strip B) in which the denaturation step was omitted, capture and specific detection on membrane strips was still observed. Moreover, the intensity of the signal generated by the non-denatured product was approximately 40–60% of that generated by the denatured product (FIG. 14). FIG. 14 is a measurement of the mean pixel density of the capture zones shown in FIG. 13, minus strip background. Negative controls, without product, were measured at a mean pixel density of zero. FIG. 14 shows the quantification of the reaction zone, after capture of the denatured and non-denatured PCR 289 product. This phenomenon of detection of non-denatured PCR product was also shown with different PCR products including the 707 bp fragment and the 99 base pair product (Sequence and primers listed in Example 6). The advantages of this lateral flow system, omitting the denaturation step are; the reduction in time, potential for automated analysis of amplified DNA directly after PCR, and reduced contamination generated by PCR aerosols.

EXAMPLE 9

Non-Specific DNA (Genomic) Does Not Preclude The Detection Of Target DNA

Example 9 shows that the inclusion of non-specific DNA does not prevent the detection of target DNA.

Target DNA from the Venezuelan equine encephalitis (VEE) was amplified with primers (Table 1, [1]) with and without 100 ng of non-specific genomic DNA. In addition the 99 base oligonucleotide was also amplified with its appropriate primers(Example 6), with and without genomic DNA. The PCR conditions were the same as previously described (GENERAL METHODS and Example 2. As controls, the PCR mixture containing the primers for the VEE was amplified without target DNA. Aliquots of the PCR products were run in the lateral flow method on membranes using the previously described methods (Example 2 and GENERAL METHODS).

FIG. 15 shows the detection of target DNA with and without genomic DNA at the reaction zone containing specific immobilized probes. Detection of the 99 base fragment was accomplished after amplification of samples, with (A) and without (B) genomic DNA. Arrow indicated the area containing the capture probes. Asterisks also indicate a second probe (complementary to the VEE 289 bp fragment) not specific for the 99 base target. Membranes (C and D) showed detection of the VEE 289 bp fragment at the reaction zone containing its specific probe both, with (C) and without (D) genomic DNA included. Samples E and F were amplified without any target DNA, with (E) and without (F) genomic DNA.

On membranes A & B (FIG. 15) the probe specific for the 99 base fragment was printed and immobilized with UV irradiation at the capture zone (arrow). In addition, on these membranes a second control probe non-specific for the 99 base target was also immobilized. The 99 base target, after hybridization with immobilized probe, was detected on the lateral flow membrane at the capture zone containing only its specific complementary probe (arrow). It was noted that there was no non-specific binding of the target DNA at a second capture zone containing the second control probe (asterisk). Despite the inclusion of 100 ng of genomic DNA (FIG. 15, membrane strip, A), the signal intensity was similar to the signal without the genomic DNA (FIG. 15 membrane strip, B without genomic DNA). Similar results were obtained with the 289 bp VEE fragments as shown (FIG. 15 membrane strips, C with genomic DNA and D without genomic DNA). There was no observable decrease in binding of the specific target DNA when samples containing genomic DNA, were compared with samples without genomic DNA. Controls (FIG. 15, membrane strips E and F) lacking target DNA showed no binding at the capture zone.

Thus the target nucleic acid in the sample hybridized specifically to its probe without any competition from non-specific DNA. Target DNA did not bind to a non-complementary probe. Genomic DNA does not preclude the detection of target DNA. Further, controls, amplified in without target DNA, showed no binding to the reaction zone. In addition, all experiments clearly showed that the target DNA hybridized specifically to the reaction zone did not bind to other regions of the test strip.

TABLE 1

| |
|---|
| [1] Amplification primers for the amplification of the Venezuelan Equine Encephalitis gene specific to yield 707 and 289 base pair fragments. |
| VE1156: 5'-GGCACGACGGTTATGTTAGAC-3' [SEQ ID NO: 22] |
| VE1281: 5'-GTGTCACTCCATACATCTCG-3' [SEQ ID NO: 23] |
| VE1569: 5'-AACTGCTGTCCACTTCTGAG-3' [SEQ ID NO: 24] |
| VE1862: 5'-CATACCTTCTGGTGCTAGAG-3' [SEQ ID NO: 25] |
| [2] Probe immobilized for hybridization on membrane to VEE target DNA: |
| 5'-TAATCCTGTAGGCAGAGAACTCTATACTCATCCCCCAGAA-3' [SEQ ID NO: 26] |
| [3] Probe immobilized on membrane to 99 base target DNA (57 mer) |
| 5' ACA GCA CCA CAG ACC ACG CAA CTC TAG AGG ATC CCG GGT ACT GTT TGT CTT CCT GCC 3' [SEQ ID NO: 27] |

We claim:

1. A method for detecting the presence of a non-denatured nucleic acid analyte in a buffered test sample, said test sample consisting of suitable amounts of a blocking agent, and non-ionic detergent, said method comprising the steps of:

(i) contacting the test sample with a first end of a test strip comprising a chromatographic material capable of moving the test sample laterally from the first end to a second end of the test strip by capillary migration and at least one single stranded capture nucleic acid molecule irreversibly affixed to the test strip at a specific capture zone, the capture nucleic acid being complementary to a portion of the nucleic acid analyte;

(ii) incubating the test strip and test sample of step (i) for at least 5 minutes, whereby the test sample is allowed to traverse at least a portion of the test strip whereby the nucleic acid analyte is captured by hybridization to the capture nucleic acid in the capture zone;

(iii) contacting the first end of the test strip with a suitable amount of wash buffer whereby unreacted nucleic acid analyte is removed from the capture zone;

(iv) contacting the test strip with a signal-generating substance such that the signal-generating substance reacts with a reporter conjugate that is located either within the nucleic acid analyte or bound to the nucleic acid analyte to produce a detectable signal at the capture zone; and (v) comparing the detectable signal at the capture zone with a signal detectable at a portion of the test strip other than at the capture zone.

2. A method for detecting the presence of a non-denatured, randomly amplified polymorphic nucleic acid analyte in a test sample, comprising the steps of:

(i) contacting the test sample with a first end of a test strip comprising a chromatographic material, the test strip having a specific capture zone in which the randomly amplified polymorphic nucleic acid analyte is immobilized;

(ii) contacting the test strip with a hybridization solution consisting essentially of suitable amounts of a blocking agent, and non-ionic detergent and containing a detection probe, the detection probe comprising a base sequence complementary with the randomly amplified polymorphic nucleic acid analyte;

(iii) incubating the test strip and test sample of step (ii) for at least five minutes whereby the test sample is allowed to traverse at least a portion of the test strip, whereby the detection probe and the randomly amplified polymorphic nucleic acid analyte hybridize;

(iv) contacting the first end of the test strip with a suitable amount of wash buffer whereby the unreacted detection probe is removed from the capture zone;

(v) contacting the test strip with a signal generating substance such that the signal generating substance reacts with a reporter conjugate located either within the detection probe or reversibly affixed to the test strip to produce a detectable signal at the capture zone; and (vi) comparing the detectable signal at the capture zone with a signal detectable at a portion of the test strip other than at the capture zone.

3. The method of claim 1 wherein said one single stranded capture nucleic acid molecule is irreversibly affixed to the test strip by means of a capture moiety.

4. The method of claim 1 where at step (iv) the reporter conjugate comprises a radioactive molecule linked to a member of a binding pair wherein said contacting is accomplished in the absence of a signal generating substance.

5. The method of claim 1 wherein the nucleic acid analyte comprises at least one reactive ligand.

6. The method of claim 1 wherein the reporter conjugate comprises a reporter moiety linked to a member of a binding pair, the reporter moiety selected from the group consisting of an enzyme, a chemiluminescent molecule, particles, and a fluorescent molecule.

7. The method of claim 6 wherein the reporter moiety is linked to an affinity-reactive member of a binding pair.

8. The method of claim 6 wherein the reporter moiety is linked to an immuno-reactive member of a binding pair, selected from the group consisting of antibodies antigens, haptens and anti-haptens.

9. The method of claim 6 wherein the reporter moiety is linked to a nucleic acid molecule capable of hybridizing to the nucleic acid analyte to be detected.

10. The method of claim 3 wherein the capture moiety is an affinity-reactive member of a binding pair.

11. The method of claim 3 wherein the capture moiety is an immuno-reactive member of a binding pair.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
          (A) LENGTH: 362 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

| | |
|---|---|
| GATCCGAGCG TTGCATATGT GGAAGAAGAT CATATTGCAC ATGAATATGC GCAATCTGTT | 60 |
| CCTTATGGCA TTTCTCAAAT TAAAGCGCCG GCTCTTCACT CTCAAGGCTA CACAGGCTCT | 120 |
| AACGTAAAAG TAGCTGTTAT CGACAGCGGA ATTGACTCTT CTCATCCTGA CTTAAACGTC | 180 |
| AGAGGCGGAG CAAGCTTCGT TCCTTCTGAA ACAAACCCAT ACCAGGACGG CAGTTCTCAC | 240 |
| GGTACGCATG TCGCCGGTAC GATTGCCGCT CTTAATAACT CAATCGGTGT TCTGGGCGTA | 300 |
| GCGCCAAGCG CATCATTATA TGCAGTAAAA GTGCTTGATT CAACAGGAAG CGGCCAATAT | 360 |
| AG | 362 |

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

| | |
|---|---|
| GATCCGAGCG TTGCATATGT G | 21 |

(2) INFORMATION FOR SEQ ID NO:3:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

| | |
|---|---|
| CTATATTGGC CGCTTCCTGT TC | 22 |

(2) INFORMATION FOR SEQ ID NO:4:

(i) SEQUENCE CHARACTERISTICS:
          (A) LENGTH: 182 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

| | |
|---|---|
| AAAAGCACAA AAATTTTTG CATCTCCCCC TTGATGACGT GGTTTACGAC CCCATTTAGT | 60 |

```
AGTCAACCGC AGTGAGTGAG TCTGCAAAAA AATGAAATTG GGCAGTTGAA ACCAGACGTT      120

TCGCCCCTAT TACAGACTCA CAACCACATG ATGACCGAAT ATATAGTGGA GACGTTTAGA      180

TG                                                                    182

(2) INFORMATION FOR SEQ ID NO:5:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:5:

GTTAGCGGAT CCAAAAGCAC AAAAAAT                                         27

(2) INFORMATION FOR SEQ ID NO:6:

(i) SEQUENCE CHARACTERISTICS:
        (A) LENGTH:  28 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:6:

AGCAGTGAAT TCCATCTAAA CGTCTCCA                                        28

(2) INFORMATION FOR SEQ ID NO:7:

(i) SEQUENCE CHARACTERISTICS:
        (A) LENGTH:  45 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:7:

TGCATCTCCC CCTTGATGAC GTGGTTTACG ACCCCATTTA GTAGT                      45

(2) INFORMATION FOR SEQ ID NO:8:

(i) SEQUENCE CHARACTERISTICS:
        (A) LENGTH:  45 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:8:

CGGCAGTTCT CACGGTACGC ATGTCGCCGG TACGATTGCC GCTCT                      45

(2) INFORMATION FOR SEQ ID NO:9:

(i) SEQUENCE CHARACTERISTICS:
        (A) LENGTH:  10 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:9:
```

```
GGAGTACTGG                                                                10
```

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GCGGTAGATG                                                                10
```

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CCAGTACTCC                                                                10
```

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GCGGTAGATG                                                                10
```

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GCGGTAGATG                                                                10
```

(2) INFORMATION FOR SEQ ID NO:14:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 99 base Target (xi) SEQUENCE DESCRIPTION: SEQ ID NO:14:

GCTTCAGCGC CACATACATC ATACAGCACC ACAGACCACG CAACTCTAGA GGATCCCGGG    60

TACTGTTTGT CTTCCTGCCT TTGCTGATGC CGCTTCTGC    99

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

GCTTCAGCGC CACATACATC AT    22

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

GCAGAAGCGG CATCAGCAAA    20

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(vi) ORIGINAL SOURCE:
        (C) INDIVIDUAL ISOLATE: apr capture probe (xi) SEQUENCE DESCRIPTION: SEQ ID NO:17:

CGGCAGTTCT CACGGTACGC ATGTAGCCGG TACGATTGCC GCTCT    45

(2) INFORMATION FOR SEQ ID NO:18:

(i) SEQUENCE CHARACTERISTICS:
        (A) LENGTH: 362 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: apr target (xi) SEQUENCE DESCRIPTION: SEQ ID NO:18:

GATCCGAGCG TTGCATATGT GGAAGAAGAT CATATTGCAC ATGAATATGC GCAATCTGTT    60

CCTTATGGCA TTTCTCAAAT TAAAGCGCCG GCTCTTCACT CTCAAGGCTA CACAGGCTCT    120

AACGTAAAAG TAGCTGTTAT CGACAGCGGA ATTGACTCTT CTCATCCTGA CTTAAACGTC    180

AGAGGCGGAG CAAGCTTCGT TCCTTCTGAA ACAAACCCAT ACCAGGACGG CAGTTCTCAC      240

GGTACGCATG TCGCCGGTAC GATTGCCGCT CTTAATAACT CAATCGGTGT TCTGGGCGTA      300

GCGCCAAGCG CATCATTATA TGCAGTAAAA GTGCTTGATT CAACAGGAAG CGGCCAATAT      360

AG                                                                    362

(2) INFORMATION FOR SEQ ID NO:19:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for dnak
            target capture"

(xi) SEQUENCE DESCRIPTION: SEQ ID NO:19:

TGCATCTCCC CCTTGATGAC GTGGTTTACG ACCCCATTTA GTAGTCAACC GC              52

(2) INFORMATION FOR SEQ ID NO:20:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: dnak target (xi) SEQUENCE DESCRIPTION: SEQ ID NO:20:

AAAAGCACAA AAAATTTTTG CATCTCCCCC TTGATGACGT GGTTTACGAC CCCATTTAGT      60

AGTCAACCGC AGTGAGTGAG TCTGCAAAAA AATGAAATTG GCAGTTGAA ACCAGACGTT       120

TCGCCCCTAT TACAGACTCA CAACCACATG ATGACCGAAT ATATAGTGGA GACGTTTAGA     180

TG                                                                    182

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "capture probe for
            99 base target"

(xi) SEQUENCE DESCRIPTION: SEQ ID NO:21:

ACAGCACCAC AGACCACGCA ACTCTAGAGG ATCCCGGGTA CTGTTTGTCT TCCTGCC         57

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "VEE 3' primer"

(xi) SEQUENCE DESCRIPTION: SEQ ID NO:22:

GGCACGACGG TTATGTTAGA C                                                  21

(2) INFORMATION FOR SEQ ID NO:23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "VEE 51 primer"

(xi) SEQUENCE DESCRIPTION: SEQ ID NO:23:

GTGTCACTCC ATACATCTCG                                                    20

(2) INFORMATION FOR SEQ ID NO:24:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "VEE 5' primer"

(xi) SEQUENCE DESCRIPTION: SEQ ID NO:24:

AACTGCTGTC CACTTCTGAG                                                    20

(2) INFORMATION FOR SEQ ID NO:25:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "VEE 3' primer"

(xi) SEQUENCE DESCRIPTION: SEQ ID NO:25:

CATACCTTCT GGTGCTAGAG                                                    20

(2) INFORMATION FOR SEQ ID NO:26:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "capture probe for
             VEE target"

(xi) SEQUENCE DESCRIPTION: SEQ ID NO:26:

TAATCCTGTA GGCAGAGAAC TCTATACTCA TCCCCCAGAA                               40

(2) INFORMATION FOR SEQ ID NO:27:

(i) SEQUENCE CHARACTERISTICS:
         (A) LENGTH: 57 base pairs
         (B) TYPE: nucleic acid
         (C) STRANDEDNESS: single
         (D) TOPOLOGY: linear (ii) MOLECULE TYPE: other nucleic acid -continued

```
    (A) DESCRIPTION:  /desc = "capture probe for
        99 base target"

(xi) SEQUENCE DESCRIPTION: SEQ ID NO:27:

ACAGCACCAC AGACCACGCA ACTCTAGAGG ATCCCGGGTA CTGTTTGTCT TCCTGCC            57
```